US010926041B2

(12) United States Patent
Oyauchi et al.

(10) Patent No.: US 10,926,041 B2
(45) Date of Patent: Feb. 23, 2021

(54) MEDICAL PUNCTURE NEEDLE AND METHOD OF MANUFACTURING PUNCTURE NEEDLE

(71) Applicant: TERUMO KABUSHIKI KAISHA, Tokyo (JP)

(72) Inventors: Tetsuya Oyauchi, Isehara (JP); Daisuke Nishiuchi, Kawagoe (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 201 days.

(21) Appl. No.: 16/234,373

(22) Filed: Dec. 27, 2018

(65) Prior Publication Data

US 2019/0125981 A1 May 2, 2019

Related U.S. Application Data

(60) Division of application No. 15/205,896, filed on Jul. 8, 2016, now Pat. No. 10,201,665, which is a (Continued)

(30) Foreign Application Priority Data

Jan. 31, 2014 (JP) .............................. JP2014-017828

(51) Int. Cl.
*B21G 1/08* (2006.01)
*A61M 5/32* (2006.01)
(Continued)

(52) U.S. Cl.
CPC .......... *A61M 5/3286* (2013.01); *A61M 5/158* (2013.01); *B21D 28/10* (2013.01);
(Continued)

(58) Field of Classification Search
CPC . B21G 1/006; B21G 1/08; B21G 1/12; B21D 3/02; B21D 11/203; B21D 28/10; B24B 5/24; B24B 9/16; A61M 5/3286
See application file for complete search history.

(56) References Cited

U.S. PATENT DOCUMENTS 3,071,135 A * 1/1963 Baldwin ............. A61M 5/3286
604/274
3,448,740 A 6/1969 Figge
(Continued)

FOREIGN PATENT DOCUMENTS

EP 0 739 640 A1 10/1996
EP 1 374 935 A1 1/2004
(Continued)

OTHER PUBLICATIONS

International Search Report for International Patent Application No. PCT/JP2014/005827 dated Mar. 3, 2015.
(Continued)

*Primary Examiner* — Edward T Tolan
(74) *Attorney, Agent, or Firm* — Foley & Lardner LLP

(57) ABSTRACT

A medical puncture needle includes an end portion including a needle tip; and a main body portion contiguous with the end portion, having a substantially circular cross-sectional outer shape. The end portion includes a first bevel formed by a curved surface, the bevel having an angle that gradually decreases toward the needle tip in an axial direction, in a cross-section orthogonal to the axial direction, relative to an imaginary plane that extends along an axis of the main body portion.

16 Claims, 15 Drawing Sheets

Related U.S. Application Data continuation of application No. PCT/JP2014/005827, filed on Nov. 19, 2014.

(51) Int. Cl.

| | | |
|---|---|---|
| *A61M 5/158* | (2006.01) | |
| *B21G 1/12* | (2006.01) | |
| *B21D 28/10* | (2006.01) | |
| *B21D 11/20* | (2006.01) | |

(52) U.S. Cl.
CPC ............... *B21G 1/08* (2013.01); *B21G 1/12* (2013.01); *A61M 2207/00* (2013.01); *B21D 11/203* (2013.01)

(56) References Cited

U.S. PATENT DOCUMENTS

| | | | | |
|---|---|---|---|---|
| 3,906,932 | A * | 9/1975 | Ayres | A61M 5/162 600/577 |
| 4,430,358 | A * | 2/1984 | Wada | B21G 1/08 128/DIG. 21 |
| 5,752,942 | A * | 5/1998 | Doyle | B24B 19/16 604/274 |
| 5,968,022 | A * | 10/1999 | Saito | B24B 19/16 604/264 |
| 6,517,523 | B1 | 2/2003 | Kaneko et al. | |
| 7,070,583 | B1 * | 7/2006 | Higuchi | A61M 5/3286 604/164.06 |
| 7,082,795 | B2 | 8/2006 | Ooyauchi | B21C 37/06 72/368 |
| 7,435,239 | B2 * | 10/2008 | Yatabe | A61M 5/158 604/272 |
| 8,328,772 | B2 * | 12/2012 | Kinast | A61M 5/3286 604/274 |
| 9,265,896 | B2 * | 2/2016 | Uemura | A61B 5/150282 |
| 2004/0030302 | A1 | 2/2004 | Kamata et al. | |
| 2005/0107751 | A1 | 5/2005 | Yatabe et al. | |
| 2005/0241357 | A1 * | 11/2005 | Ooyauchi | B21C 37/083 72/368 |
| 2010/0257711 | A1 * | 10/2010 | Ferguson | B24B 19/16 29/9 |
| 2013/0118420 | A1 * | 5/2013 | Toyoda | C22F 1/10 122/235.14 |
| 2013/0218102 | A1 * | 8/2013 | Iwase | A61M 5/00 604/272 |
| 2015/0183076 | A1 * | 7/2015 | Lange | B24B 5/24 451/11 |

FOREIGN PATENT DOCUMENTS

| | | |
|---|---|---|
| EP | 1 491 225 A1 | 12/2004 |
| FR | 1225009 A | 6/1960 |
| JP | 2000-262615 A | 9/2000 |
| JP | 2003-290354 A | 10/2003 |
| JP | 2007-054194 A | 3/2007 |
| WO | WO 2012/073947 A1 | 6/2012 |

OTHER PUBLICATIONS

Japanese Office Action Translation dated May 15, 2018 in corresponding application No. JP2015-559625.
European Search Report dated Aug. 7, 2017 from related EP Application No. 14880929.6. (7 pages).
International Search Report dated Mar. 3, 2015 in PCT/JP2014/005827.
International Preliminary Report on Patentability dated Aug. 2, 2016 in PCT/JP2014/005827.
Written Opinion of the International Searching Authority dated Mar. 3, 2015 in PCT/JP2014/005827.
Carrieri, Translation of FR 1225009, 1960.

* cited by examiner

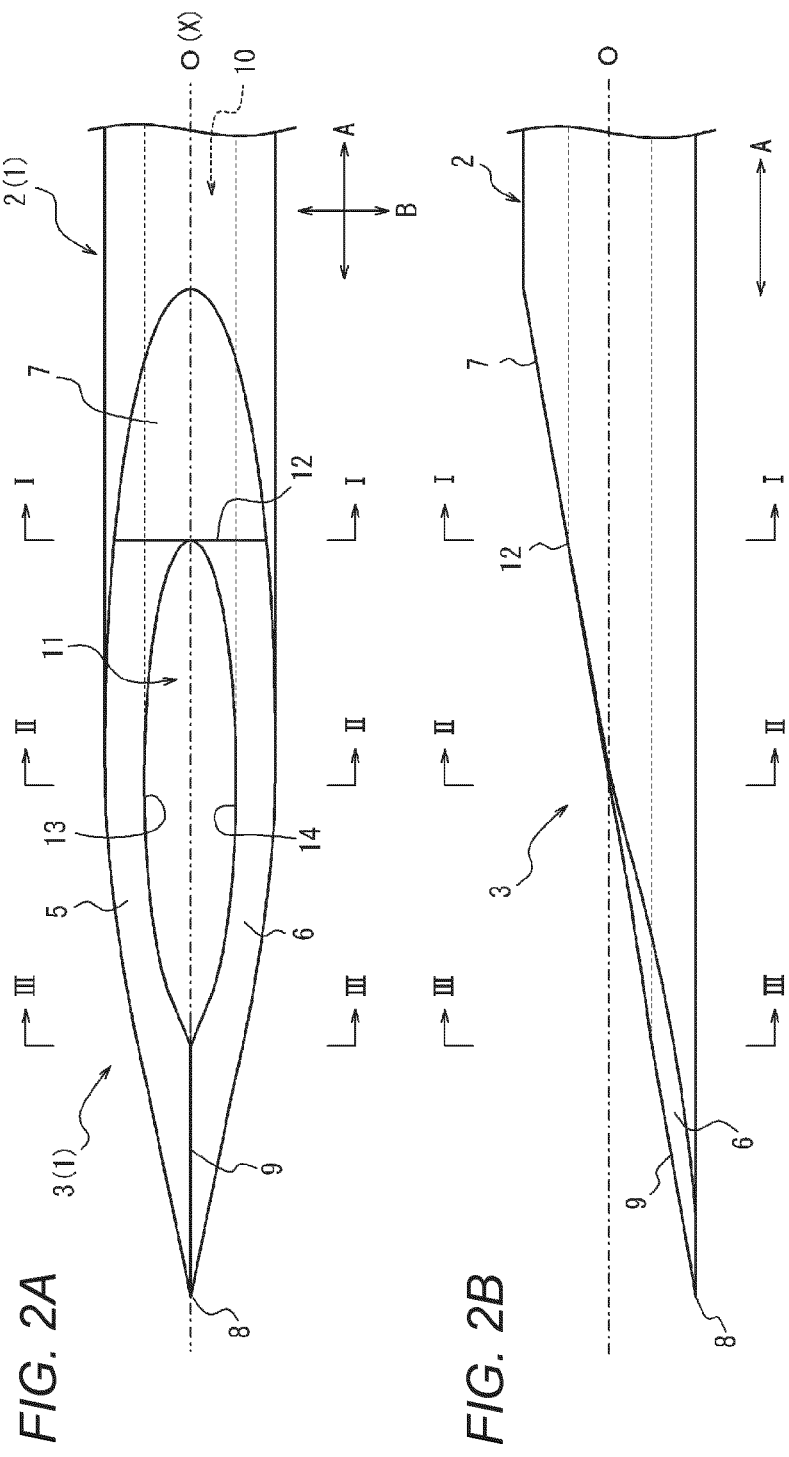

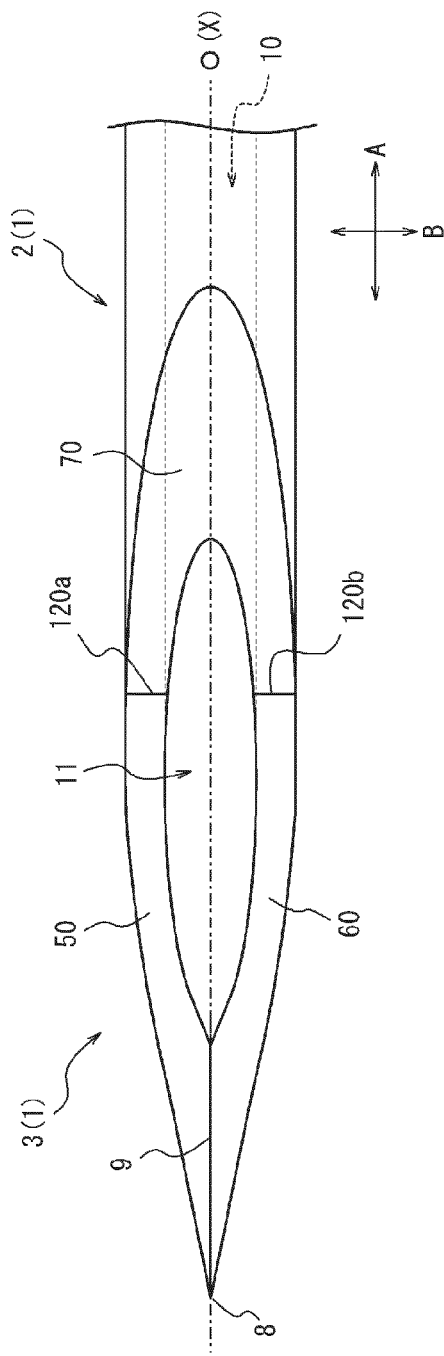

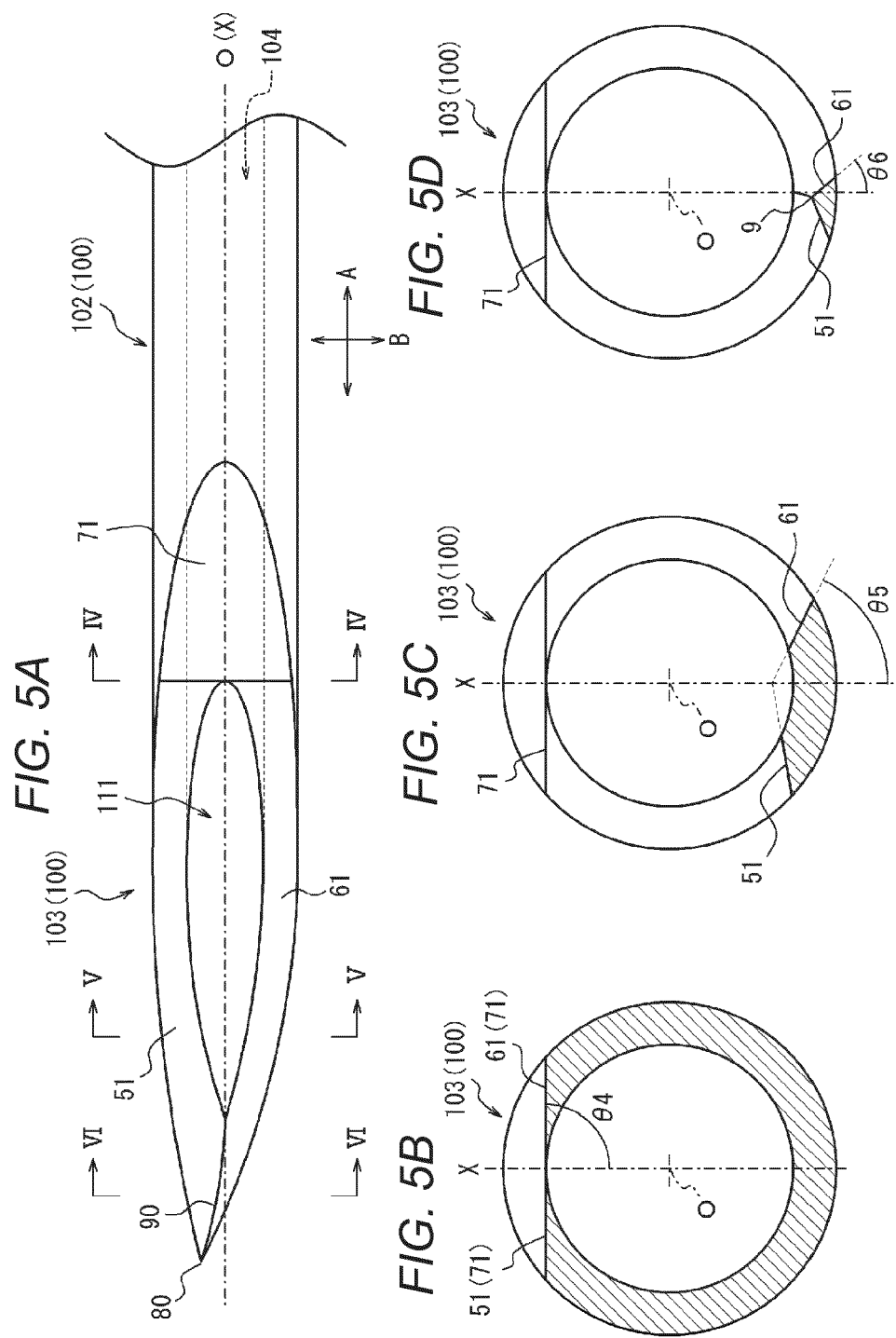

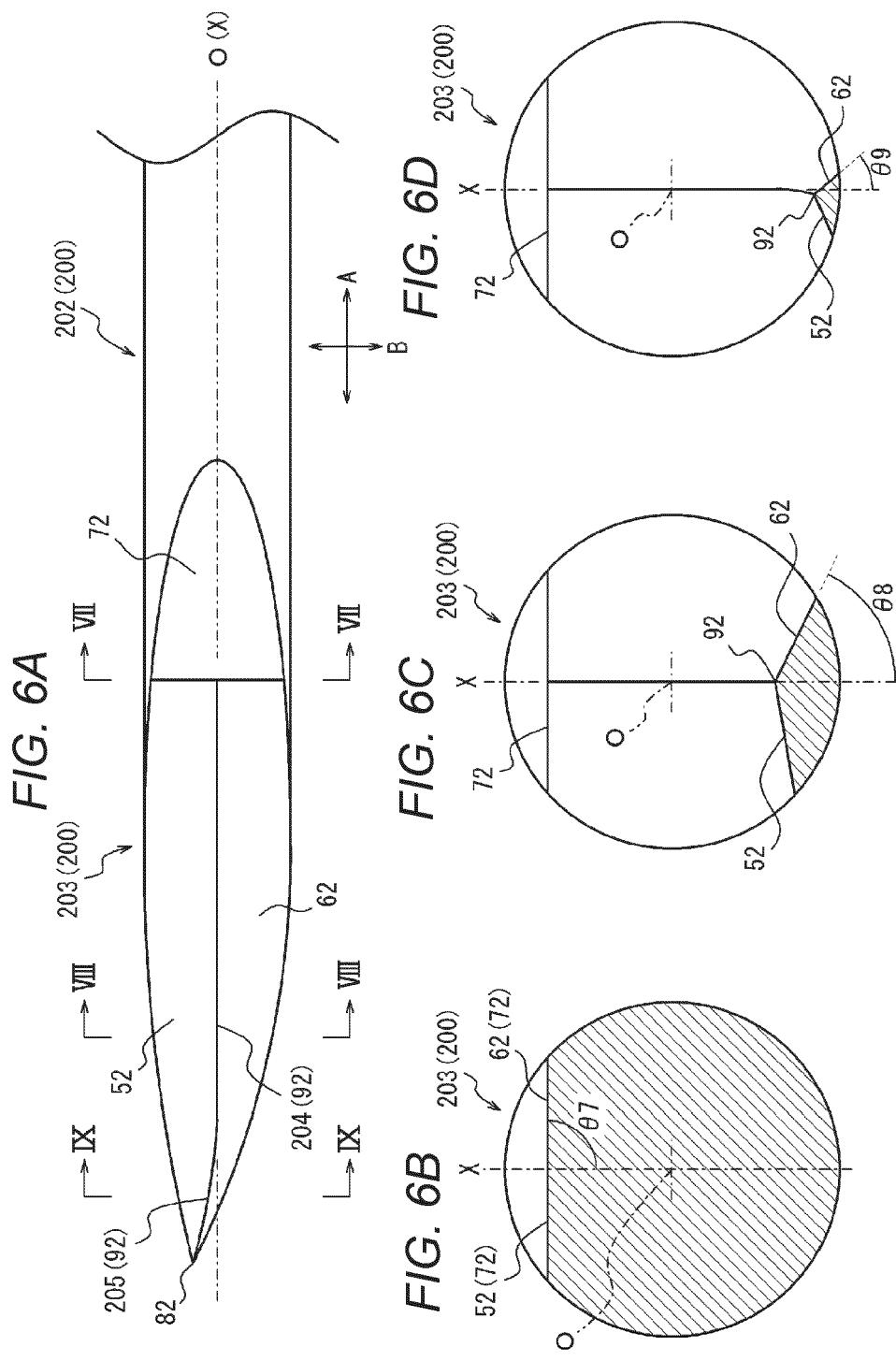

MEDICAL PUNCTURE NEEDLE AND METHOD OF MANUFACTURING PUNCTURE NEEDLE

CROSS-REFERENCE TO RELATED APPLICATIONS

This application is a divisional of U.S. patent application Ser. No. 15/205,896, filed on Jul. 8, 2016, which is a continuation application of and claims the benefit of priority from International Patent Application No. PCT/JP2014/005827, filed Nov. 19, 2014, which claims priority to Japanese Patent Application No. 2014-017828, filed on Jan. 31, 2014. The contents of these applications are incorporated herein by reference in their entireties.

BACKGROUND

The present disclosure relates to a medical puncture needle and a method of manufacturing puncture needles.

It is known for a medical puncture needle, such as a blood sampling needle or an indwelling needle used for infusion, to include an end portion having a plurality of bevels of different angles in a longitudinal direction of the puncture needle, in order to alleviate pain caused during insertion of the puncture needle into human body.

As the puncture needle, a needle for an injection syringe is disclosed in JP 2000-262615 A ("JP '615"). The needle of JP '615 includes a taper-shaped tip portion formed by cutting a tip portion of a cylindrical main body obliquely at one side thereof, the needle includes a first slanted surface contiguous to an outer peripheral surface of the cylindrical main body and formed at a predetermined angle with respect to an axis of the main body, a second slanted surfaces contiguous to the first slanted surface and formed at a larger angle with respect to the axis of the main body than the angle of the first slanted surface, and a third slanted surface contiguous to the second slanted surface and contiguous to a cutting edge tip, the third slanted surfaces being formed at a larger angle with respect to the axis of the main body than the angle of the second slanted surfaces.

SUMMARY

Technical Problem

An injection needle having an end portion formed by connecting a plurality of slanted surfaces having different angles with respect to a longitudinal direction, as in ce '615, can alleviate the pain caused during insertion of the injection needle into human body. However, a configuration having connection between the plurality of slanted surfaces of different angles with respect to a longitudinal direction forms a ridge at a connection between the plurality of slanted surfaces, the ridge generates puncture resistance during insertion of the injection needle, and a patient's pain or the like may not be fully reduced.

Embodiments of the present invention have been made in view of the above problems, and an object of certain embodiments of the present invention is to provide a medical puncture needle having a beveled shape unlikely to form a ridge constituted by a plurality of bevels and causing puncture resistance, and to provide a method of manufacturing the puncture needle.

Solution to Problem

According to a first aspect of the present invention, a medical puncture needle includes an end portion including a needle tip, and a main body portion contiguous with the end portion, having a substantially circular cross-sectional outer shape, and the end portion includes a bevel formed by a curved surface, having an angle gradually reduced relative to one imaginary plane including an axis of the main body portion, toward the needle tip in the axial direction, in a cross-section orthogonal to the axial direction.

According to an embodiment of the present invention, preferably, the bevel includes curved first and second bevels the first and second bevels having a cutting edge constituted by a ridge formed wherein the first and second bevels intersect, defining the needle tip as one end, and at least one of the first and second bevels has an angle gradually reduced relative to the imaginary plane in a cross-section orthogonal to the axis of the main body, toward the needle tip in the axial direction.

According to an embodiment of the present invention, preferably, the end portion includes an inclined surface contiguous with the first and second bevels and constituted by a flat surface inclined with respect to the axis, and the imaginary plane is a plane perpendicular to the inclined surface and including the axis.

According to an embodiment of the present invention, preferably, the needle tip is not positioned on the plane perpendicular to the inclined surface and including the axis.

According to an embodiment of the present invention, the puncture needle has a hollow portion defined to extend from the main body portion to the end portion, and in the end portion, the first and second bevels each have an inner edge defining an opening at one end of the hollow portion in the axial direction.

According to an embodiment of the present invention, the angle preferably has a constant change rate per unit length in the axial direction.

According to a second aspect of the present invention, a method of manufacturing a medical puncture needle includes forming a bevel at one end portion of a linear member by wire cutting, while rotating the linear member having a substantially circular cross-sectional outer shape about an axis of the linear member in one direction, and moving the linear member in one direction to be inclined by a predetermined angle relative to the axial direction of the linear member.

According to an embodiment of the present invention, when defining the bevel as a first bevel, a second bevel and a cutting edge are preferably formed by wire cutting, while rotating the linear member about the axis in a direction opposite to the one direction and moving the linear member in the one direction inclined relative to the axial direction of the linear member by the predetermined angle or in a direction opposite to the one direction. The second bevel is formed at a position of the one end portion different from a position of the first bevel, and the cutting edge is constituted by a ridge formed where the first and second bevels inersect each other, having a needle tip.

Advantageous Effects of Invention

According to the present invention, the medical puncture needle having a beveled shape unlikely to form a ridge constituted by a plurality of bevels and causing the puncture resistance, and the method of manufacturing the puncture needle.

BRIEF DESCRIPTION OF THE DRAWINGS

FIG. 1A is a top plan view, FIG. 1B is a side view, FIG. 1C is a bottom plan view, and FIG. 1D is a perspective view.

FIGS. 2A and 2B are partial enlarged views of the puncture needle of FIGS. 1A and 1B.

FIG. 4 is a diagram illustrating a first bevel, a second bevel, and an inclined surface which have shapes different from those illustrated in FIGS. 1A to 1D, and are selected from first bevels, second bevels, and inclined surfaces applicable to the present invention.

FIGS. 5A to 5D are diagrams illustrating a puncture needle according to an embodiment of the present invention. FIG. 5A is a top plan view, FIG. 5B is a cross-sectional view taken along a line IV-IV of FIG. 5A, FIG. 5C is a cross-sectional view taken along a line V-V of FIG. 5A, and FIG. 5D is a cross-sectional view taken along a line VI-VI of FIG. 5A.

FIGS. 6A to 6D are diagrams illustrating a puncture needle according to an embodiment of the present invention. FIG. 6A is a top plan view, FIG. 6B is a cross-sectional view taken along a line VII-VII of FIG. 6A, FIG. 6C is a cross-sectional view taken along a line VIII-VIII of FIG. 6A, FIG. 6D is a cross-sectional view taken along a line IX-IX of FIG. 6A.

FIGS. 7A, 7B, 7C, and 7D are a top plan view, a side view, a bottom plan view, and a perspective view, respectively.

FIG. 14B is a cross-sectional view taken along a line X-X of FIG. 14A.

DETAILED DESCRIPTION

Hereinafter, a medical puncture needle and a method of manufacturing the puncture needle will be described according to embodiments of the present invention, with reference to FIGS. 1A to 1D to FIG. 15. Note that, in figures, common members are denoted by the same reference signs.

First Embodiment

Figure 1A:
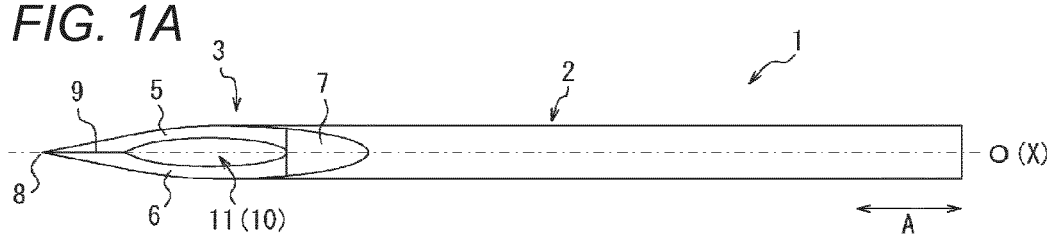
FIGS. 1A to 1D are diagrams illustrating a puncture needle according to an embodiment of the present invention.
Figure 1B:
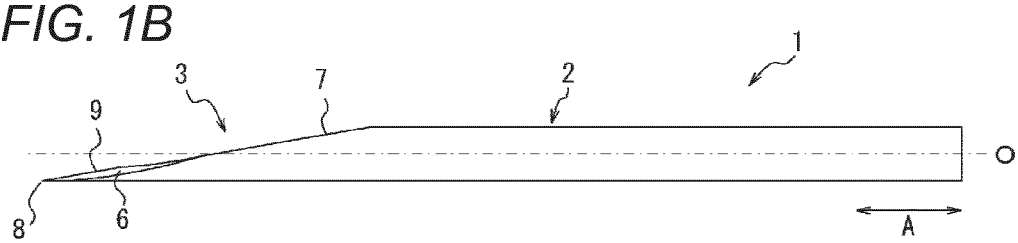
Figure 1C:
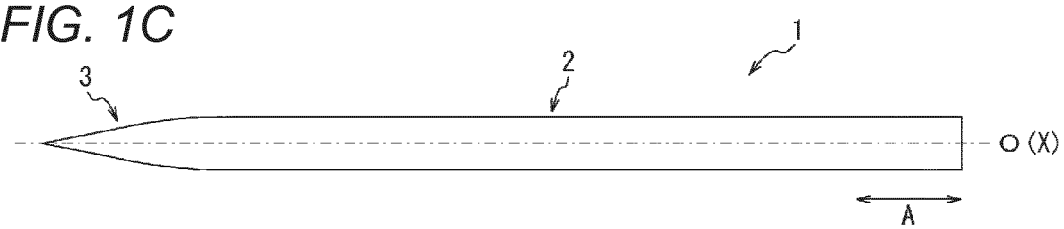
Figure 1D:
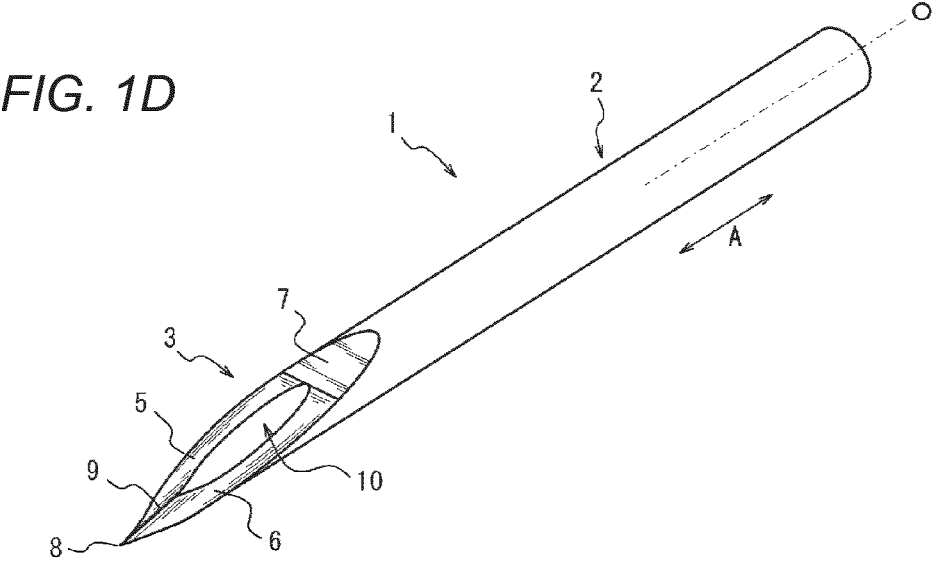

First, a puncture needle 1 will be described as the medical puncture needle according to an embodiment of the present invention. FIGS. 1A to 1D are diagrams illustrating the puncture needle 1. Specifically, FIG. 1A is a top plan view of the puncture needle 1, FIG. 1B is a side view of the puncture needle 1, and FIG. 1C is a bottom plan view of the puncture needle 1. FIG. 1D is a perspective view of the puncture needle 1.

As illustrated in FIGS. 1A to 1D, the puncture needle 1 includes a main body portion 2 and an end portion 3, and defines a hollow portion 10 extending from the main body portion 2 to the end portion 3.

The main body portion 2 is a tubular body contiguous with the end portion 3 and having a substantially circular cross-sectional outer shape. Here, "cross-sectional" and "cross-sectional outer shape" represent a cross-section orthogonal to an axis O of the main body portion 2.

As illustrated in FIGS. 1A to 1D, the end portion 3 includes a first bevel 5 and a second bevel 6 as a bevel constituted by a curved surface, and an inclined surface (third bevel) 7 as a bevel constituted by a flat surface. Further, the first bevel 5 and the second bevel 6 have a ridge formed wherein the bevels intersect, and the ridge forms a cutting edge 9 having a needle tip 8 at one end. Note that "needle tip" represents an end in an axial direction A of the axis O of the main body portion 2 (hereinafter, simply referred to as "axial direction A").

Specifically, the inclined surface 7 is a flat surface inclined with respect to the axial direction A. The inclined surface 7 is contiguous with an outer peripheral surface of the main body portion 2, on the main body portion 2 side in the axial direction A, and contiguous with the first bevel 5 and the second bevel 6 on the needle tip 8 side in the axial direction A.

Both of the first bevel 5 and the second bevel 6 are contiguous with the inclined surface 7 on the main body portion 2 side in the axial direction A, and cross each other on the needle tip 8 side to form the ridge, that is, the cutting edge 9. Further, the first bevel 5 and the second bevel 6 according to the present embodiment define an opening 11 being one end on the end portion 3 side of the hollow portion 10.

As can be seen from a side view of FIG. 1B, the second bevel 6 has an angle changed according to the position in the axial direction A, in cross-sections orthogonal to the axial direction A. Specifically, in FIG. 1B, although only an outer edge of the second bevel 6 can be visually confirmed at a position in the axial direction A where the second bevel 6 is contiguous with the inclined surface 7, the second bevel 6 can be visually confirmed at a position in the axial direction A where the cutting edge 9 is formed. That is, the second bevel 6 is formed by a curved surface, for example a helical surface.

The curved surface extends while being twisted from the position where the second bevel 6 is contiguous with the inclined surface 7 to the needle tip 8 in the axial direction A. Note that, similarly to the second bevel 6, the first bevel 5 is also formed by a curved surface extending while being twisted from a position where the first bevel 5 is contiguous with the inclined surface 7 to the needle tip 8 in the axial direction A.

Figure 3C:
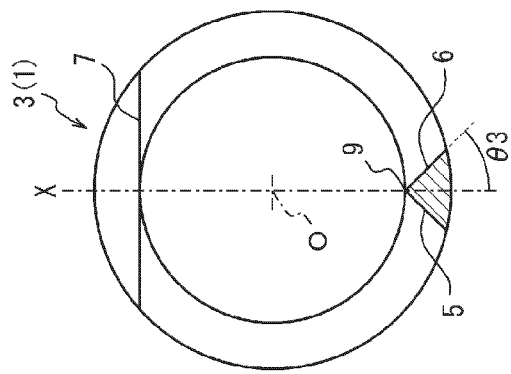
FIGS. 3A, 3B, and 3C are a cross-sectional view taken along a line I-I of FIGS. 2A and 2B, a cross-sectional view taken along a line II-II, and a cross-sectional view taken along a line III III, respectively.
Figure 3B:
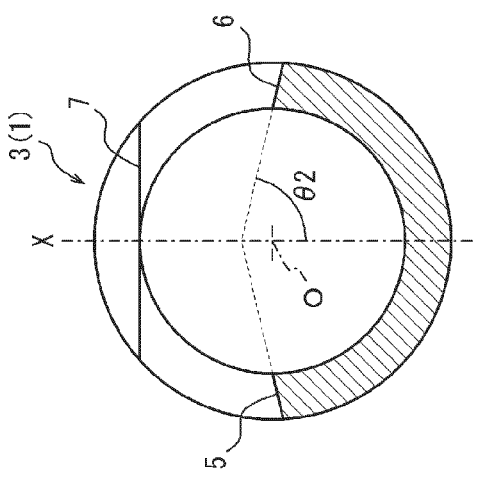
Figure 3A:
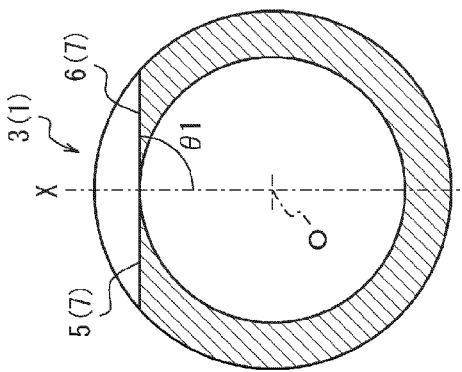

In other words, when one imaginary plane is set including the axis O of the main body portion 2, the end portion 3 includes the first bevel 5 and the second bevel 6 constituted by the curved surfaces each having an angle θ gradually reduced relative to the one imaginary plane in the cross-sections orthogonal to the axial direction A toward the needle tip 8 in the axial direction A (see FIGS. 3A to 3C or the like). That is, the puncture needle 1 according to the present embodiment is a puncture needle allowing definition of such one imaginary plane.

Note that since the puncture needle 1 according to the present embodiment has a plurality of planes which can be defined as the "imaginary plane", a plane X perpendicular to the inclined surface 7 and including the axis O (hereinafter, simply referred to as "axial plane X") is defined as the "imaginary plane", for convenience of description. However, it is also apparent that for example a plane including the cutting edge 9 and the axis O (a plane identical to the axial plane X in the present embodiment) or the like can be defined as the "imaginary plane". Furthermore, a definition of only one of such imaginary planes is preferably required, and the puncture needle is not limited to such a configuration having a plurality of planes as described in the present embodiment.

Curved surface shapes of the first bevel 5 and the second bevel 6 will be described later in detail (see FIGS. 3A to 3C or the like).

In the present invention, "end portion" represents one end portion of the puncture needle having the bevel, and "main body portion" represents a portion of the puncture needle having no bevel. Thus, the end portion 3 according to the present embodiment is a portion of an integral rod-shaped member constituting the puncture needle 1, and the portion has the first bevel 5, the second bevel 6, and the inclined surface (third bevel) 7 in the axial direction A. Furthermore, the main body portion 2 according to the present embodiment is a portion of the integral rod-shaped member constituting the puncture needle 1, and the portion has a substantially circular cross-sectional outer shape, and does not have the first bevel 5, the second bevel 6, and the inclined surface (third bevel) 7 in the axial direction A.

As a material of the puncture needle 1 according to the present embodiment, a metal material, such as stainless steel, aluminum or an aluminum alloy, or titanium or a titanium alloy, can be employed.

Configurations and characteristic portions according to the present embodiment will be described below in detail.

[Main Body Portion 2]

The main body portion 2 according to the present embodiment has a tubular body in which an inner peripheral surface has a uniform inner diameter and the outer peripheral surface has a uniform outer diameter, in the axial direction A, and an end portion opposite to the end portion 3 in the axial direction A is connected to a medical device such as a syringe.

Note that, in the present embodiment, the rod-shaped member constituting the whole puncture needle 1 has an inner peripheral surface (the inner peripheral surface of the main body portion 2 and an inner peripheral surface of the end portion 3) defining the hollow portion 10, and in the rod-shaped member, the inner peripheral surface has a uniform inner diameter and an outer peripheral surface has a uniform outer diameter, in the axial direction A, but the rod-shaped member is not limited to this configuration. For example, the inner diameter of the inner peripheral surface of the rod-shaped member and the outer diameter of the outer peripheral surface of the rod-shaped member may be gradually reduced toward the end portion 3, in the central axis direction A (see FIGS. 8 to 15). Further, for example, the rod-shaped member can have an outer diameter having a tapered shape gradually reduced toward the end portion 3 in the axial direction A, and an inner diameter being uniform in the axial direction A. Still further, for example, a portion having an inner diameter gradually reduced or gradually increased toward the end portion 3 in the axial direction A can be provided in an area in the axial direction A. The inner diameter and the outer diameter of the rod-shaped member constituting the puncture needle 1 can have various configurations according to the use or the like of the puncture needle 1.

[Inclined Surface 7 in End Portion 3]

FIGS. 2A and 2B are enlarged views of the end portion 3 of FIGS. 1A and 1B, respectively. FIGS. 3A, 3B, and 3C are a cross-sectional view taken along a line I-I of FIGS. 2A and 2B, a cross-sectional view taken along a line II-II, and a cross-sectional view taken along a line III-III, respectively.

As illustrated in FIGS. 2A and 2B, the inclined surface 7 is a flat surface inclined in the axial direction A, a portion of the inclined surface 7 on the main body portion 2 side is contiguous with the outer peripheral surface of the main body portion 2, and a portion of the inclined surface 7 on the needle tip 8 side is contiguous with the first bevel 5 and the second bevel 6. Note that an inclination angle of the inclined surface 7 in the axial direction A is larger than that of an outer wall of the main body portion 2 in the axial direction A in a cross-section including the axis O. In the present embodiment, the outer diameter of the rod-shaped member constituting the puncture needle 1 is uniform in the axial direction A, and the rod-shaped member has an outer wall extending parallel with the axial direction A when viewed in a cross-section including the axis O. Thus, when the inclined surface 7 is inclined with respect to the axial direction A, the inclination angle of the inclined surface 7 is larger than the inclination angle of the outer wall of the main body portion 2. However, when the rod-shaped member constituting the puncture needle 1 has an outer diameter gradually reduced or gradually increased toward the end portion 3 in the axial direction A, the inclined surface 7 is inclined with respect to the outer wall of the main body portion 2 in the cross-section including the axis O, as well as inclined in the axial direction A.

Here, the inclined surface 7 according to the present embodiment has an outer edge on the needle tip 8 side in the axial direction A, and, as illustrated in FIG. 2 (a), the outer edge extends in a direction B orthogonal to the axial direction A (hereinafter, simply referred to as "orthogonal direction B") That is, a ridge 12 formed at a position where the inclined surface 7 is contiguous with the first bevel 5 and the second bevel 6 extends in the orthogonal direction B.

Furthermore, the ridge 12 is located at a position adjacent to the opening 11 in the axial direction A. That is, as illustrated in FIG. 2 (a), the puncture needle 1 defining the opening 11 has an inner edge, and a position of the inner edge on the main body portion 2 side in the axial direction A is part of the ridge 12.

Note that, as illustrated in FIG. 2 (a), the cutting edge 9 according to the present embodiment extends on the axial plane X. Further, the needle tip 8 being one end of the cutting edge 9 is also positioned on the axial plane X.

[First Bevel 5 and Second Bevel 6 in End Portion 3]

As illustrated in FIG. 2 (a) the first bevel 5 and the second bevel 6 are contiguous with the inclined surface 7 on the main body portion 2 side in the axial direction A. More specifically, the first bevel 5 and the second bevel 6 are contiguous with the inclined surface 7 on both sides of the axial plane X. FIG. 3A is the cross-section taken along the line I-I, that is, a cross-section orthogonal to the axial direction A, located at a position where the first bevel 5 and the second bevel 6 are connected to the inclined surface 7 in the axial direction A. As illustrated in FIG. 3A, in the cross-section taken along the line I-I, each of the first bevel 5 and the second bevel 6 has an angle θ1 of 90 degrees relative to the axial plane X. In other words, in the cross-section taken along the line I-I, each of the first bevel 5 and the second bevel 6 linearly extends in a direction orthogonal to the axial plane X (coincident with the ridge 12).

FIG. 3B is the cross-section taken along the line II-II, that is, a cross-section orthogonal to the axial direction A, located at a position where there is the opening 11 in the axial direction A. As illustrated in FIG. 3B, in the cross-section taken along the line II-II, each of the first bevel 5 and the second bevel 6 has an angle θ2 relative to the axial plane X, and the angle θ2 is an acute angle smaller than the angle θ1.

FIG. 3C is the cross-section taken along the line that is, a cross-section orthogonal to the axial direction A, located at a position where the cutting edge 9 is formed in the axial direction A. As illustrated in FIG. 3C, in the cross-section taken along the line each of the first bevel 5 and the second bevel 6 has an angle θ3 relative to the axial plane X, and the angle θ3 is an acute angle smaller than the angle θ1 and the angle θ2.

As described above, each of the first bevel 5 and the second bevel 6 is a straight line when viewed in a cross-section orthogonal to the axial direction A, each of the first bevel 5 and the second bevel 6 according to the present embodiment has the angle θ relative to the axial plane X in the cross-section orthogonal to the axial direction A, and the angle θ is gradually reduced toward the needle tip 8 (coming closer to the needle tip 8) in the axial direction A. Note that although the angles θ1 to θ3 of the second bevel 6 relative to the axial plane X are illustrated in FIGS. 3A to 3C, the first bevel 5 also has angles relative to the axial plane X, similar to the angles θ1 to θ3 of the second bevel 6. Further, three cross-sections of FIGS. 3A to 3C are used as an example showing a magnitude relationship between the angles θ1, θ2, and θ3, and establishment of the magnitude relationship between the angles θ is not applied only to these three cross-sections.

Accordingly, as described in the present embodiment, the first bevel 5 and the second bevel 6 can be contiguous with the inclined surface 7 so that a large level difference is not formed relative to the outer edge of the inclined surface 7 on the needle tip 8 side in the axial direction A, at a connecting position with the inclined surface 7 (see FIG. 3A). Further, as described in the present embodiment, the first bevel 5 and the second bevel 6 are opposed and changed in direction toward the needle tip 8 in the axial direction A from the position of the cross-section taken along the line I-I, and cross each other at a position on the needle tip 8 side relative to the opening 11 in the axial direction A to form the cutting edge 9 (see FIGS. 3B and 3C).

The puncture needle 1 according to the present embodiment includes the first bevel 5 and the second bevel 6 having such curved surface shapes, the ridge 12 formed between the bevels and the inclined surface 7 is inhibited from causing the puncture resistance during insertion of the puncture needle 1 into human body. Thus, when the puncture needle 1 is inserted into human body, a pain felt by a patient or the like into which the puncture needle 1 is inserted can be further reduced.

In the present embodiment, the angle θ of each of the first bevel 5 and the second bevel 6 has a constant angle change rate per unit length in the axial direction A. Thus, the first bevel 5 and the second bevel 6 each formed by a helical surface smoothly twisted from the connecting position with the inclined surface 7 toward the needle tip 8 further inhibit formation of a ridge likely to cause the puncture resistance during insertion into human body.

Furthermore, in the present embodiment, an inner edge 13 of the first bevel 5 and an inner edge 14 of the second bevel 6 define the opening 11 at one end of the hollow portion 10 in the axial direction A, as illustrated in FIG. 2 (a). The opening 11 according to the present embodiment is defined only by the inner edge 13 of the first bevel 5 and the inner edge 14 of the second bevel 6, but the opening 11 is not limited to such a configuration. For example, as illustrated in FIG. 4, the connecting position between the first and second bevels 50 and 60 and the inclined surface 70 may be provided in an area in the axial direction A at which the opening 11 is positioned, that is, a connecting position 120a between the first bevel 50 and the inclined surface 70 and a connecting position 120b between the second bevel 60 and the inclined surface 70 may be provided at positions across the opening 11 in the orthogonal direction B, to form the opening 11 by the edges of the first bevel 50, the second bevel 60, and the inclined surface 70.

[Cutting Edge 9 in End Portion 3]

The cutting edge 9 has the ridge formed where the first bevel 5 and the second bevel 6 intersect, as described above. Furthermore, as described above, the cutting edge 9 according to the present embodiment extends on the axial plane X, and the needle tip 8 being one end of the cutting edge 9 is positioned on the axial plane X. That is, the puncture needle 1 according to the present embodiment is a hollow needle having a configuration symmetric about the axial plane X.

As described in the present embodiment, a configuration in which the puncture needle 1 has an acute tip and is provided with the cutting edge 9 causes the cutting edge 9 or the outer edge of the first bevel 5 and the outer edge of the second bevel 6 in the vicinity of the cutting edge 9 to cut skin during insertion of the puncture needle 1 into human body, and resistance on skin can be reduced during insertion of the puncture needle 1. Thus, the pain felt by the patient or the like into which the puncture needle 1 is inserted can be further reduced.

Here, as described above, the angles θ of the first bevel 5 and the second bevel 6 (see FIGS. 3A to 3C) are gradually reduced toward the needle tip 8 in the axial direction A. This configuration is similarly applied to an area where the cutting edge 9 is positioned in the axial direction A. That is, in the cutting edge 9, the angle θ is gradually reduced from one end on the main body portion 2 side in the axial direction A toward the needle tip 8 along the cutting edge 9. Accordingly, in the puncture needle 1 according to the present embodiment, a configuration in the vicinity of the needle tip 8 can be made acute compared with a configuration having a uniform angle θ in the area in which the cutting edge 9 extends in the axial direction A, and thus, the pain of the patient or the like can be further reduced during insertion of the puncture needle 1.

Furthermore, according to the present embodiment, the whole of the cutting edge 9 and the needle tip 8 are configured to be positioned on the axial plane X, but the whole or part of the cutting edge 9 and the needle tip 8 may be configured not to be positioned on the axial plane X. This configuration will be described below as a second embodiment.

Second Embodiment

Next, a puncture needle 100 according to an embodiment of the present invention will be described below. The puncture needle 100 has a cutting edge and a needle tip different in configuration from those of the puncture needle 1 according to the first embodiment. Specifically, in the first embodiment, the whole of the cutting edge 9 and the needle tip 8 of the puncture needle 1 are positioned on the axial plane X, but, in the present embodiment, part of the cutting edge 90 and the needle tip 80 of the puncture needle 100 are not positioned on the axial plane X. Note that a configuration different from that of the puncture needle 1 according to the first embodiment will be mainly described here.

The puncture needle 100 in which part of the cutting edge 90 is not positioned on the axial plane X is illustrated in FIGS. 5A to 5D. Specifically, FIG. 5A is a top plan view of the puncture needle 100, FIG. 5B is a cross-sectional view taken along a line IV-IV of FIG. 5A, FIG. 5C is a cross-sectional view taken along a line V-V of FIG. 5A, and FIG. 5D is a cross-sectional view taken along a line VI-VI of FIG. 5A.

As illustrated in FIG. 5A, the puncture needle 100 includes a main body portion 102 and an end portion 103, and defines a hollow portion 104 extending from the main body portion 102 to the end portion 103. Further, as illustrated in FIGS. 5A to 5D, the end portion 103 includes a first bevel 51, a second bevel 61, and an inclined surface 71. Further, the first bevel 51 and the second bevel 61 have a ridge formed where the bevels intersect, and the ridge forms a cutting edge 90 having a needle tip 80 at one end.

As illustrated in FIGS. 5A to 5D, in the axial direction A, one end of the cutting edge 90 on the main body portion 102 side is positioned on the axial plane X, similarly to the cutting edge 9 in the puncture needle 1 according to the first embodiment. However, the cutting edge 90 is formed to be gradually increased in distance from the axial plane X toward the needle tip 80 in the axial direction A. In other words, the cutting edge 90 according to the present embodiment is a curved cutting edge receding from the axial plane X to the first bevel 51 in the orthogonal direction B (upper side in FIG. 5A), toward the needle tip 80 in the axial direction A. Thus, the needle tip 80 is not positioned on the axial plane X. In the present embodiment, as illustrated in FIG. 5A, the cutting edge 90 is entirely constituted by the curved cutting edge, but the cutting edge 90 is not limited to this configuration, and may be entirely constituted by a linear cutting edge. Further, the cutting edge 90 may have a cutting edge only partially having a curved portion. Still further, the cutting edge 90 may have a cutting edge only partially having a straight portion. In the cutting edge 90 according to the present embodiment, one end on the main body portion 102 side in the axial direction A is positioned on the axial plane X, but the cutting edge may be formed so that the one end does not cross the axial plane X.

Because the cutting edge 90 and the needle tip 80 are configured as illustrated in FIG. 5A, as a portion making contact with skin is formed not making into a pointed shape but into substantially a linear shape when applying the needle tip 80 of the puncture needle 100 to the skin, a force applied to the skin is dispersed. Accordingly, the needle tip 80 configured not to be positioned on the axial plane X, as in the puncture needle 100, can reduce a sharp pain felt by the patient or the like upon contact of an acute needle tip with the skin, compared with the needle tip 8 configured to be positioned on the axial plane X as in the puncture needle 1 according to the first embodiment.

Note that, in the puncture needle 100 illustrated in FIG. 5A, a position and a shape of the cutting edge 90 and a position of the needle tip 80 are different from a position and shape of the cutting edge 9 of the puncture needle 1 according to the first embodiment and a position of the needle tip 8, but, as illustrated in FIGS. 5B to 5D, the first bevel 51 and the second bevel 61 are each have a curved surface changed in inclination direction in cross-sections orthogonal to the axial direction A, toward the needle tip 80 in the axial direction A, similarly to the first bevel 5 and the second bevel 6 of the puncture needle 1.

Specifically, FIG. 5B is the cross-section taken along the line IV-IV, that is, a cross-section orthogonal to the axial direction A, located at a position where the first bevel 51 and the second bevel 61 are connected to the inclined surface 71 in the axial direction A. As illustrated in FIG. 5B, in the cross-section taken along the line IV-IV, each of the first bevel 51 and the second bevel 61 has an angle θ4 of 90 degrees relative to the axial plane X. In other words, in the cross-section taken along the line IV-IV, each of the first bevel 51 and the second bevel 61 linearly extends in a direction orthogonal to the axial plane X.

FIG. 5C is the cross-section taken along the line V-V, that is, a cross-section orthogonal to the axial direction A, located in an area where there is the opening 111 in the axial direction A. As illustrated in FIG. 5C, in the cross-section taken along the line V-V, each of the first bevel 51 and the second bevel 61 has an angle θ5 relative to the axial plane X, and the angle θ5 is an acute angle smaller than the angle θ4.

FIG. 5D is the cross-section taken along the line VI-VI, that is, a cross-section orthogonal to the axial direction A, located at a position where the cutting edge 90 is formed in the axial direction A. As illustrated in FIG. 5D, in the cross-section taken along the line VI-VI, each of the first bevel 51 and the second bevel 61 has an angle θ6 relative to the axial plane X, and the angle θ6 is an acute angle smaller than the angle θ4 and the angle θ5.

As described above, each of the first bevel 51 and the second bevel 61 has the angle θ relative to the axial plane X, the angle θ is configured to be gradually reduced toward the needle tip 80 in the axial direction A. More specifically, the first bevel 51 and the second bevel 61 are each constituted by a helical surface twisted in the axial direction A.

However, as illustrated in FIG. 5A, since the cutting edge 90 of the puncture needle 100 does not extend on the axial plane X, an angle θ of the first bevel 51 or an angle θ of the second bevel 61 can be considered to have a configuration not to be gradually reduced toward the needle tip 80 in the axial direction A depending on an extending direction of the cutting edge 90, but neither an angle θ of the first bevel 51 nor an angle θ of the second bevel 61 has a configuration not to be gradually reduced toward the needle tip 80 in the axial direction A. That is, at least one of the first bevel 51 and the second bevel 61 has the angle θ configured to be gradually reduced toward the needle tip 80 in the axial direction A. Note that, in FIGS. 5B to 5D, the second bevel 61 has the angle θ including the angles θ4 to θ6 as an example, but the first bevel 51 also has the angle θ configured to be gradually reduced toward the needle tip 80 in the axial direction A. Further, three cross-sections of FIGS. 5B to 5D are used as an example showing a magnitude relationship between the angles θ4, θ5, and θ6, and establishment of the magnitude relationship between the angles θ is not applied only to these three cross-sections.

Similarly to the above-mentioned puncture needle 1 according to the first embodiment, the axial plane X set as one imaginary plane including the axis O is described also in the present embodiment, but, for example, a plane including the axis O and passing through the needle tip 80 can be set as the one imaginary plane including the axis O. That is, in the cross-section orthogonal to the axial direction A, at least one of the first bevel 51 and the second bevel 61 has the angle relative to the plane including the axis O and passing through the needle tip 80, and the angle is configured to be gradually reduced toward the needle tip 80 in the axial direction A.

Third Embodiment

Next, a puncture needle 200 according to an embodiment of the present invention will be described below. The puncture needle 200 is a solid needle, and different from the puncture needle 100 according to the second embodiment in the absence of the hollow portion. A difference from the puncture needle 100 according to the second embodiment will be mainly described here.

The puncture needle 200 as the solid needle without a hollow portion is illustrated in FIGS. 6A to 6D, Specifically, FIG. 6A is a top plan view of the puncture needle 200, FIG. 6B is a cross-sectional view taken along a line VII-VII of FIG. 6A, FIG. 6C is a cross-sectional view taken along a line VIII-VIII of FIG. 6A, and FIG. 6D is a cross-sectional view taken along a line IX-IX of FIG. 6A.

As illustrated in FIG. 6A, the puncture needle 200 according to the present embodiment includes a main body portion 202 and an end portion 203. However, the puncture needle 200 is the solid needle without a hollow portion defined to extend from the main body portion 202 to the end portion 203. As illustrated in FIGS. 6A to 6D, the end portion 203 includes a first bevel 52, a second bevel 62, and an inclined surface 72. Furthermore, the first bevel 52 and the second bevel 62 have a ridge formed where the bevels intersect, and the ridge forms an cutting edge 92 having a needle tip 82 at one end.

The cutting edge 92 according to the present embodiment has a ridge formed where the first bevel 52 and the second bevel 62 intersect, and extending to the needle tip 82 from an outer edge of the inclined surface 72 on the needle tip 82 side in the axial direction A. Specifically, as illustrated in FIG. 6A, the cutting edge 92 includes a straight portion 204 positioned on the main body portion 202 side in the axial direction A, and a curved portion 205 positioned on the needle tip 82 side in the axial direction A to be contiguous with the straight portion 204, having the needle tip 82 at one end. The straight portion 204 extends on the axial plane X. The curved portion 205 is curved to be gradually increased in distance from the axial plane X (distance in the orthogonal direction B) toward the needle tip 82 in the axial direction A. In other words, the curved portion 205 according to the present embodiment extends to recede from the axial plane X to the first bevel 52 in the orthogonal direction B (upper side in FIG. 6A), toward the needle tip 82 in the axial direction A. Thus, the needle tip 82 is not positioned on the axial plane X, similar to the puncture needle 100 according to the second embodiment.

Note that, in the present embodiment, as illustrated in FIG. 6A, the cutting edge 92 is constituted by the straight portion 204 and the curved portion 205, but the cutting edge 92 is not limited to this configuration, and may be entirely formed into a linear shape to have a linear cutting edge, or may be entirely formed into a curved shape to have a curved cutting edge. Further, the straight portion 204 and the curved portion 205 may be reversed in position in the axial direction A. Still further, in the cutting edge 92 according to the present embodiment, the straight portion 204 is configured to be positioned on the axial plane X, but the straight portion 204 may be configured not to be entirely positioned on the axial plane X, or the straight portion 204 may be only partially positioned on the axial plane X.

The cutting edge 92 and the needle tip 82 configured as illustrated in FIG. 6A can reduce the sharp pain felt by the patient or the like upon contact of the acute needle tip with the skin, similarly to the above-mentioned puncture needle 100 according to the second embodiment.

Next, description will be made of the angles θ of the first bevel 52 and the second bevel 62 relative to the axial plane X in a cross-section orthogonal to the axial direction A. The first bevel 52 and the second bevel 62 are each constituted by a curved surface having an inclination direction changed to gradually reduce the angle θ toward the needle tip 82 in the axial direction A, similarly to the first bevel 51 and the second bevel 61 of the puncture needle 100.

Specifically, FIG. 6B is the cross-section taken along the line VII-VII, that is, a cross-section orthogonal to the axial direction A, located at a position where the first bevel 52 and the second bevel 62 are connected to the inclined surface 72 in the axial direction A. As illustrated in FIG. 6B, in the cross-section taken along the line VII-VII, each of the first bevel 52 and the second bevel 62 has an angle θ7 of 90 degrees relative to the axial plane X, and in the cross-section, each of the first bevel 52 and the second bevel 62 linearly extends in a direction orthogonal to the axial plane X.

FIG. 6C is a cross-section taken along the line VIII-VIII. As illustrated in FIG. 6C, in the cross-section taken along the line VIII-VIII, each of the first bevel 52 and the second bevel 62 has an angle θ8 relative to the axial plane X, and the angle θ8 is an acute angle smaller than the angle θ7.

FIG. 6D is a cross-section taken along the line IX-IX. As illustrated in FIG. 6D, in the cross-section taken along the line IX-IX, each of the first bevel 52 and the second bevel 62 has an angle θ9 relative to the axial plane X, and the angle θ9 is an acute angle smaller than the angle θ7 and the angle θ8.

As described above, each of the first bevel 52 and the second bevel 62 has the angle θ relative to the axial plane X, the angle θ is configured to be gradually reduced toward the needle tip 82 in the axial direction A. More specifically, the first bevel 52 and the second bevel 62 are each constituted by a helical surface twisted in the axial direction A.

Note that, in FIGS. 6B to 6D, the second bevel 62 has the angle θ including the angles θ7 to θ9 as an example, but the first bevel 52 also has the angle θ configured to be gradually reduced toward the needle tip 82 in the axial direction A.

However, the angles θ of the first bevel 52 and the second bevel 62 are not limited to the configuration gradually reduced toward the needle tip 82 in the axial direction A, and at least one of the first bevel 52 and the second bevel 62 preferably has an angle θ configured to be gradually reduced toward the needle tip 82 in the axial direction A. Similarly to the above-mentioned puncture needle 100 according to the second embodiment, the axial plane X set as one imaginary plane including the axis O is described also in the present embodiment, but, another plane can be set, for example, a plane including the axis O and passing through the needle tip 82 can be set as the one imaginary plane including the axis O.

Fourth Embodiment

Next, a puncture needle 300 according to an embodiment of the present invention will be described below. The puncture needle 300 not including a surface corresponding to the inclined surface 7 is different from the puncture needle 1 according to the first embodiment which is configured to include the inclined surface 7. A difference between the puncture needle 300 according to the present embodiment and the puncture needle 1 according to the first embodiment will be mainly descried here, and description about configurations common between them will be omitted.

FIGS. 7A to 7D are diagrams illustrating the puncture needle 300 according to the present embodiment. Specifically, FIGS. 7A, 7B, 7C, and 7D are a top plan view, a side view, a bottom plan view, and a perspective view of the puncture needle 300, respectively.

As illustrated in FIGS. 7A to 7D, the puncture needle 300 includes a main body portion 302 and an end portion 303, and defines a hollow portion 304 extending from the main body portion 302 to the end portion 303. Further, as illustrated in FIGS. 7A to 7D, the end portion 303 includes a first bevel 53 and a second bevel 63. Further, the first bevel 53 and the second bevel 63 have a ridge formed wherein the bevels intersect, and the ridge forms an cutting edge 93 having a needle tip 83 at one end.

The puncture needle 300 according to the present embodiment has a bevel including the first bevel 53 and the second bevel 63, and does not include the third bevel corresponding to the inclined surface 7 of the puncture needle 1 according to the first embodiment. Thus, the cutting edge 93 according to the present embodiment includes a first cutting edge 93a positioned on the cutting edge tip 83 side relative to an opening 311 in the axial direction A, and a second cutting edge 93b positioned on the main body portion 302 side relative to the opening 311 in the axial direction A. In other words, the first cutting edge 93a is a ridge formed where ends of the first bevel 53 and the second cutting edge 63 intersect on the needle tip 83 side in the axial direction A, and the second cutting edge 93b is a ridge formed where ends of the first bevel 53 and the second cutting edge 63 intersect on the main body portion 302 side in the axial direction A.

The first cutting edge 93a is similar to the cutting edge 9 according to the first embodiment, and similar description thereof will be omitted here.

The second cutting edge 93b is a linear ridge extending on the axial plane X, similar to the first cutting edge 93a, and is an extension of the first cutting edge 93a. The second cutting edge 93b functions to cut skin during insertion of the puncture needle 300 into human body, similarly to the first cutting edge 93a. That is, a configuration including the second cutting edge 93b can inhibit the increase of the puncture resistance at an edge of the opening 311 positioned on the main body portion 302 side in the axial direction A, during insertion of the puncture needle 300 into human body. Thus, the pain felt by the patient or the like into which the puncture needle 300 is inserted can be further reduced.

Figure 7A:
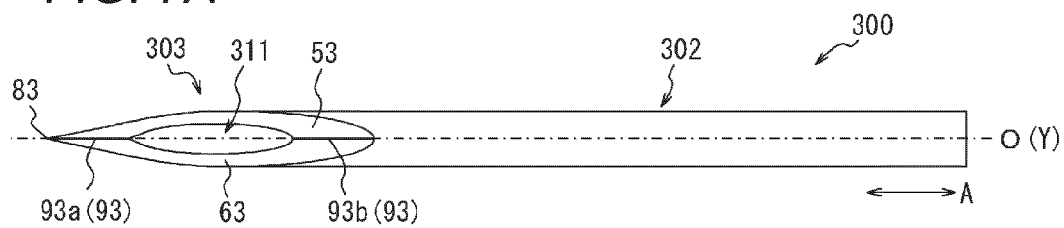
FIGS. 7A to 7D are diagrams illustrating a puncture needle according to an embodiment of the present invention.
Figure 7B:
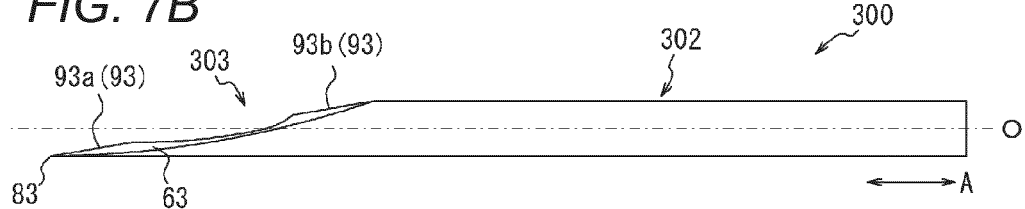
Figure 7C:
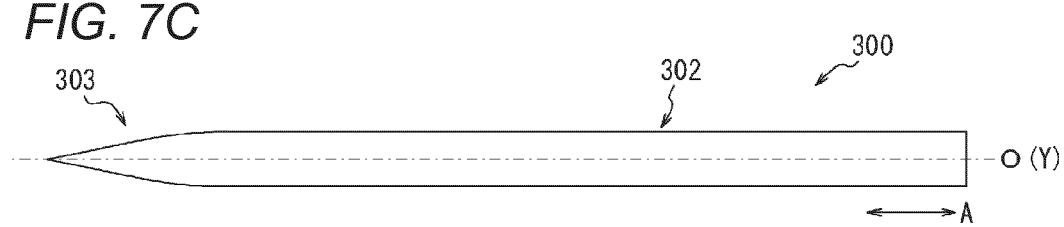
Figure 7D:
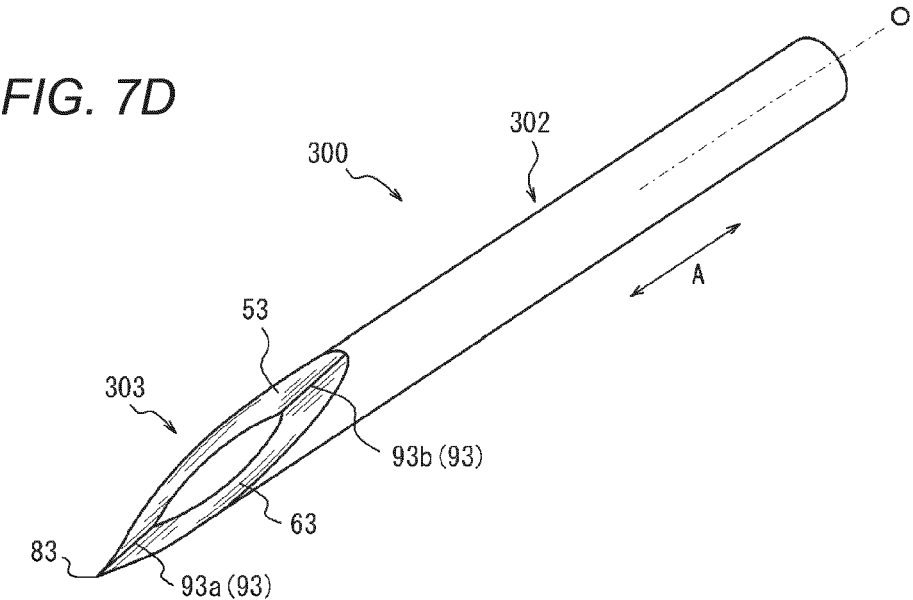

Next, surface shapes of the first bevel 53 and the second bevel 63 will be described below. As illustrated in FIG. 7B, the second bevel 63 has a visual confirmation range increasing toward the needle tip 83 in the axial direction A. That is, the second bevel 63 is a helical surface having a surface shape changed to be twisted toward the needle tip 83 in the axial direction A. Note that, in FIG. 7B, only the second bevel 63 can be visually confirmed, but the first bevel 53 is also a helical surface having a surface shape changed to be twisted toward the needle tip 83 in the axial direction A.

Here, the puncture needle 300 according to the present embodiment does not have the surface corresponding to the inclined surface 7 according to the first embodiment, so that the axial plane X cannot be defined as one imaginary plane. Therefore, in the present embodiment, a plane Y including the first cutting edge 93a and the axis O is set as the one imaginary plane for convenience of description.

In this configuration, in a cross-section orthogonal to the axial direction A, each of the first bevel 53 and the second bevel 63 has an angle relative to the plane Y, and the angle is configured to be gradually reduced toward the needle tip 83 in the axial direction A.

As described above, the puncture needle according to the present invention can be achieved by various specific configurations, and is not limited to the configurations described in the first to fourth embodiments. The puncture needles 100, 200, and 300 according to the second, third, and fourth embodiments have been described mainly in terms of a difference from any preceding embodiment, for convenience of description, but it is also apparent that the configurations according to the first to fourth embodiments are allowed to be variously combined to configure another puncture needle. For example, in the second embodiment, the configuration including three bevels of the first bevel 51, the second bevel 61, and the inclined surface 71 has been described, but for example a configuration including only two bevels of the first bevel and the second bevel maybe employed, as in the fourth embodiment. The same configuration is applied to the bevels according to the third embodiment. Further, as described in the first embodiment, the inclined surface 71 according to the second embodiment can be configured so that a connecting position between the first bevel 51 and the inclined surface 71 and a connecting position between the second bevel 61 and the inclined surface 71 are provided at a position across the opening 111 in the orthogonal direction B (a configuration similar to a positional relationship between the connecting positions 120a and 120b in FIG. 4). Still further, the needle tip 83 according to the fourth embodiment may not be on the axial plane X as in the puncture needles 100 and 200 according to the second and third embodiments. As described above, combining the configurations described in the embodiments for provision of a new puncture needle is encompassed in the technical scope of the present invention.

Fifth Embodiment

Figure 8:
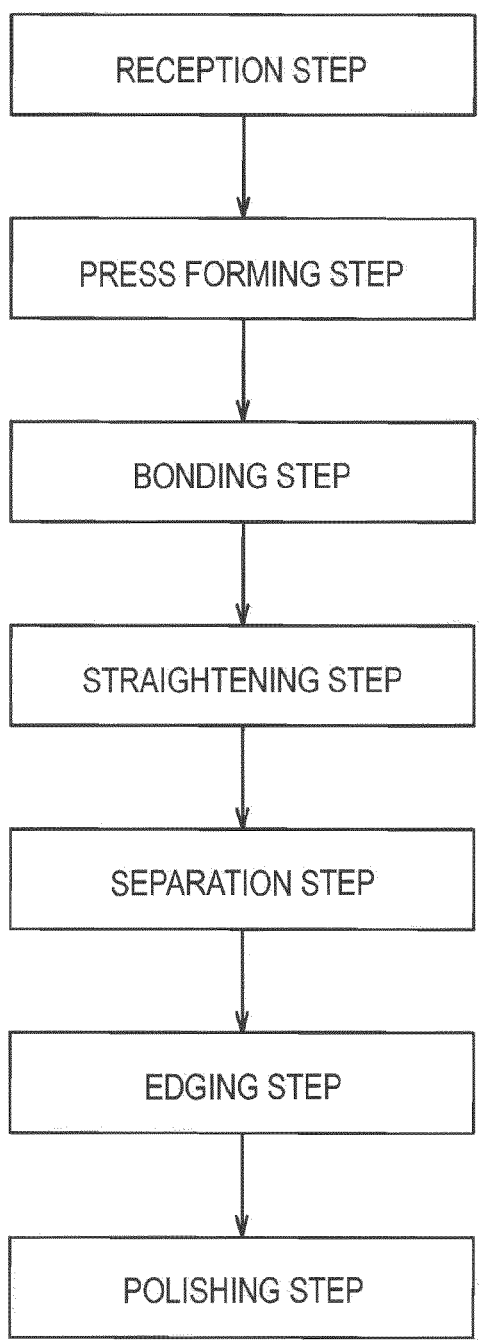
FIG. 8 is a flowchart illustrating a method of manufacturing a puncture needle according to an embodiment of the present invention.
Figure 9:
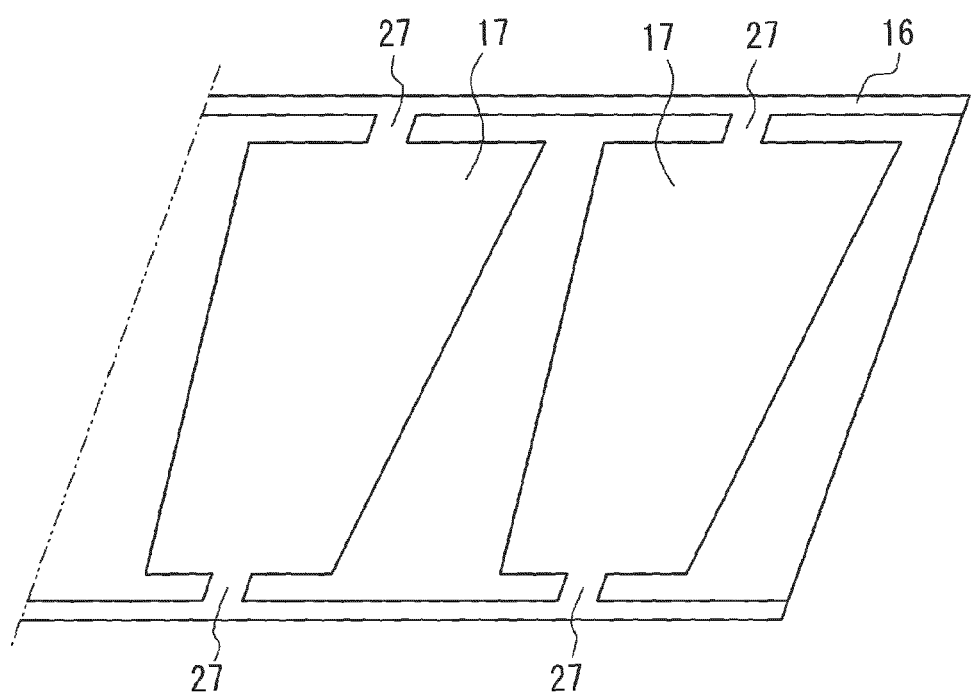
FIG. 9 is a diagram illustrating a press forming step of the method of manufacturing a puncture needle illustrated in FIG. 8.
Figure 10:
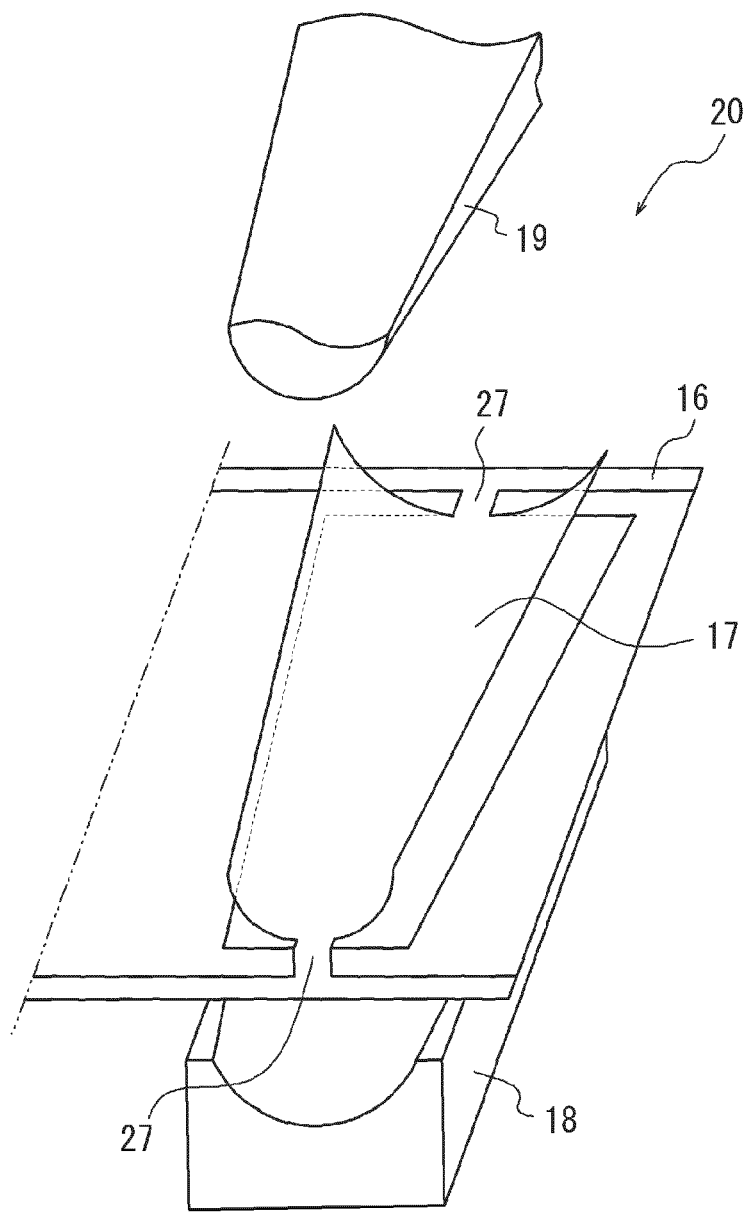
FIG. 10 is a diagram illustrating a press forming step of the method of manufacturing a puncture needle illustrated in FIG. 8.
Figure 11:
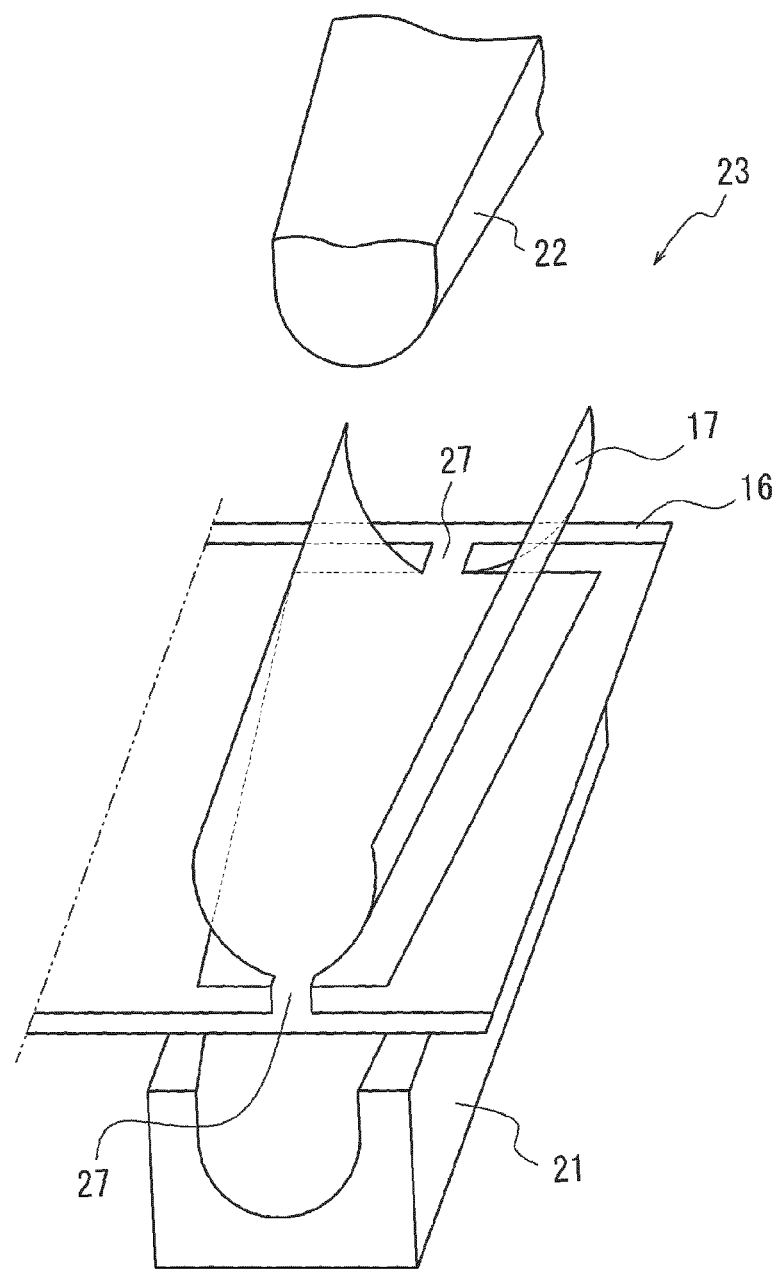
FIG. 11 is a diagram illustrating a press forming step of the method of manufacturing a puncture needle illustrated in FIG. 8.
Figure 15:
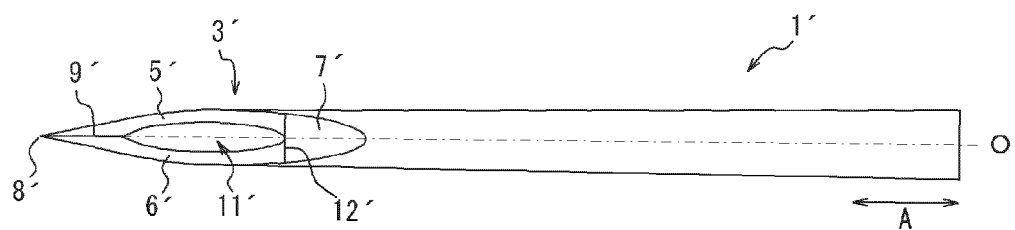
FIG. 15 is a top plan view of a puncture needle according to an embodiment of the present invention.

Last, a method of manufacturing a puncture needle 1' will be described as an embodiment of the present invention. FIG. 15 is a top plan view of the puncture needle 1'. The method of manufacturing the puncture needle 1' is described here, but the puncture needle 1' is an embodiment of the present invention, and different from the puncture needle 1 described in the first embodiment, in configuration in which a rod-shaped member constituting the puncture needle 1' has an outer diameter gradually reduced toward the end portion. The puncture needle 1' is similar to the puncture needle 1 according to the first embodiment, excluding this difference, and similar description thereof will be omitted here. Note that, in FIG. 15, portions common with those of the puncture needle 1 according to the first embodiment are denoted by reference numerals common with those of FIG. 1A with symbols "'" (dash). The method of manufacturing the puncture needle 1' will be described below in detail. FIG. 8 is a flowchart illustrating a process of manufacturing the puncture needle 1'.

As illustrated in FIG. 8, the method of manufacturing the puncture needle 1' includes a reception step of receiving a strip-shaped metal sheet member in a press forming machine, a press forming step of continuously press-forming the sheet member by the press forming machine, obtaining tubular bodies 15a as a plurality of rod-shaped members 15 partially connected to the sheet member (see FIGS. 9 to 12), a bonding step of bonding a seam of a tubular body 15a by welding or with an adhesive, a straightening step of straightening a shape of the tubular body 15a so that the tubular body has a substantially linear axis, a separation step of separating the tubular body 15a from the sheet member (see FIG. 13), a bevel forming step of forming a bevel at least at one end of the tubular body 15a by wire electric discharge machining (wire cutting), forming a puncture body 1 (see FIGS. 14A and 14B), and a polishing step of polishing the puncture body 1 by ion etching.

[Reception Step]

The strip-shaped metal sheet member is received in the press forming machine, not illustrated. In this state, a movement mechanism moves the sheet member to the press forming machine along the longitudinal direction thereof, and a shaped portion of the sheet member is positioned at a shaping position of the press forming machine. That is, first, a portion of the sheet member from which a blank is punched out is put at a position of a punching unit of the press forming machine punching out the blank. The blank and the punching unit will be described later. Note that a material of the sheet member includes, for example, a metal material such as stainless steel, aluminum or an aluminum alloy, or titanium or a titanium alloy, similarly to the material of the puncture needle 1.

[Press Forming Step]

Figure 12:
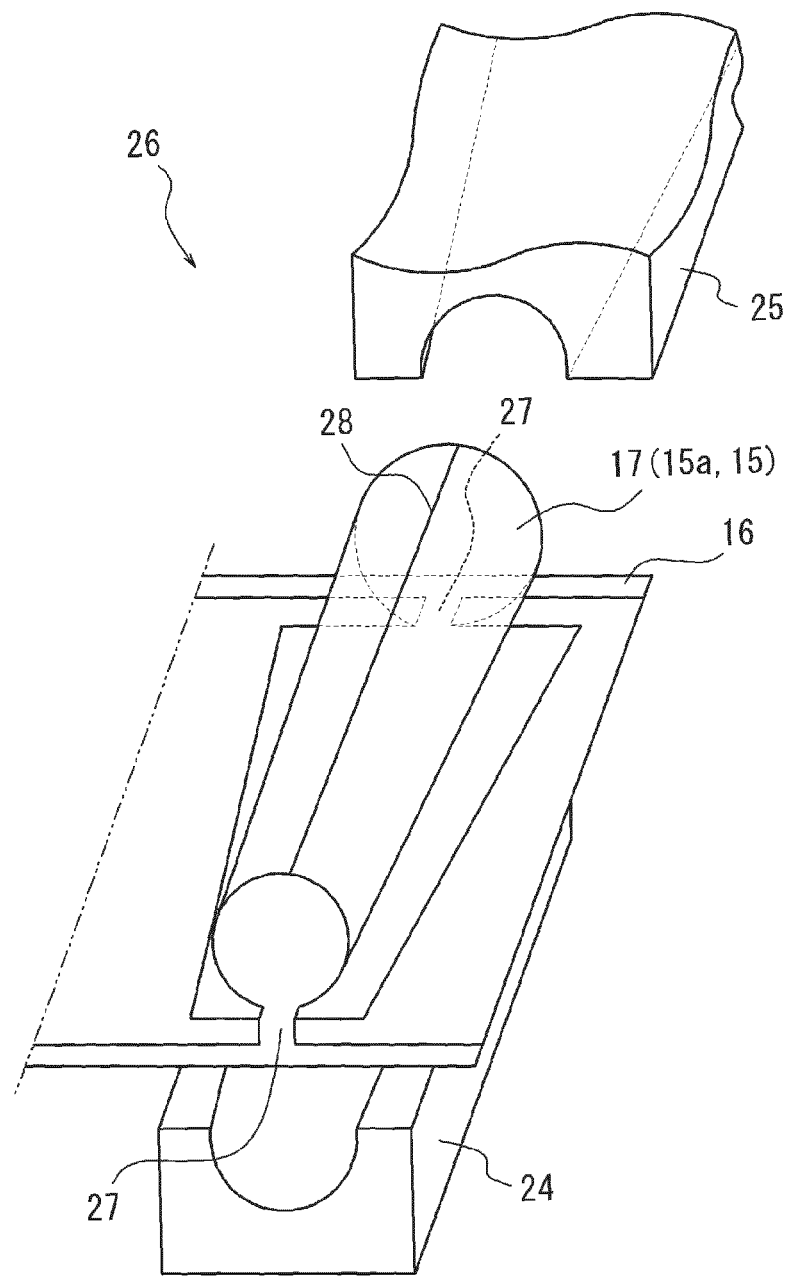
FIG. 12 is a diagram illustrating a press forming step of the method of manufacturing a puncture needle illustrated in FIG. 8.

The press forming step includes a first step and a second step. In the first step, the blank having an expanded shape of the tubular body 15a partially connected to the sheet member is punched out of the sheet member by the press forming machine, and in the second step, the blank is bent at least once by the press forming machine, using a projecting die and a recessed die, and shaped into a tubular shape to obtain the tubular body 15a partially connected to the sheet member. As illustrated in FIG. 12, in the present embodiment, the tubular body 15a has an inner diameter and an outer diameter which are maximum at one end and minimum at the other end, and the inner diameter and the outer diameter are gradually reduced from the one end to the other end.

As illustrated in FIGS. 9 to 12, as the press forming machine, a continuous press forming machine is used which has the punching unit, a first bending unit 20, a second bending unit 23, and a third bending unit 26. The punching unit mechanically punches out, from the sheet member 16, the blank 17 having the expanded shape of the tubular body 15a partially connected to the sheet member 16, the first bending unit 20 bends the blank 17 punched out by the punching unit, using a recessed die (die) 18 and a projecting die (die) 19, the second bending unit 23 further bends the blank 17 bent by the first bending unit 20, using a recessed die (die) 21 and a projecting die (die) 22, and a third bending unit 26 further bends the blank 17 bent by the second bending unit 23 into a tubular shape, using a pair of recessed dies (die) 24 and 25 having a shape corresponding to the outer shape of the tubular body 15a.

In the present embodiment, a connection portion 27 connecting the end portion of the tubular body 15a having a larger diameter to the sheet member 16, may be deformed toward a lower side in FIGS. 9 to 12 to move the end portion of the tubular body 15a having the larger diameter to the lower side in FIGS. 9 to 12 by a predetermined amount, so that an axis of the tubular body 15a and a surface of the sheet member 16 are positioned substantially parallel with each other. Further, a connection portion 27 connecting the end portion of the tubular body 15a having a smaller diameter to the sheet member 16 may be deformed toward an inside in FIGS. 9 to 12 to move the end portion of the tubular body 15a having a smaller diameter to the upper side in FIGS. 9 to 12 by a predetermined amount, and to move the end portion of the tubular body 15a having the larger diameter to the lower side in FIGS. 9 to 12 by a predetermined amount, for provision of the axis of the tubular body 15a and the surface of the sheet member 16 positioned substantially parallel with each other. Still further, in the present embodiment, the third bending unit 26 may be configured to be positioned between the recessed die 24 and the recessed die 25, further have a core (die) having a shape corresponding to an inner shape of the tubular body 15a, put the core to be positioned in a hollow portion of the tubular body 15a, and press-form the blank 17 to be bent into a tubular shape. In the present embodiment, mechanical punching is used to punch out the blank 17 from the sheet member 16, but punching is not limited to this, and, for example, punching with laser or the like may be adopted.

[Bonding Step]

In the bonding step, a portion corresponding to the seam 28 of each tubular body 15a (see FIG. 12) is bonded by welding or with an adhesive. Thus, the portion corresponding to the seam 28 of the tubular body 15a is bonded firmly and liquid-tightly. Since the tubular body 15a is made of metal, and the outer diameter of the tubular body 15a is relatively small, bonding by welding is preferably selected from bonding by welding and bonding with an adhesive, in this configuration. In welding, a bonded portion (the portion corresponding to the seam 28) is preferably fused and welded including a base material.

For welding, various types of welding (welding methods) can be used, but, for example, laser welding such as carbon dioxide laser welding, YAG laser welding, or excimer laser welding is preferably employed, and particularly, the carbon dioxide laser welding or the YAG laser welding is preferably employed, which is inexpensive and suitable for fine processing.

[Straightening Step]

In straightening, the shape of each tubular body 15a is straightened so that the axis of each tubular body 15a is made substantially straight. In this step, for example, a pair of rollers spaced apart by a predetermined distance is used to put and pass the tubular body 15a between the pair of rollers. Thus, the tubular body 15a is straightened by being pressed between the rollers, and the axis of the tubular body 15a is made substantially straight. Note that the straightening step may be performed through a method different from the present embodiment.

[Separation Step]

Figure 13:
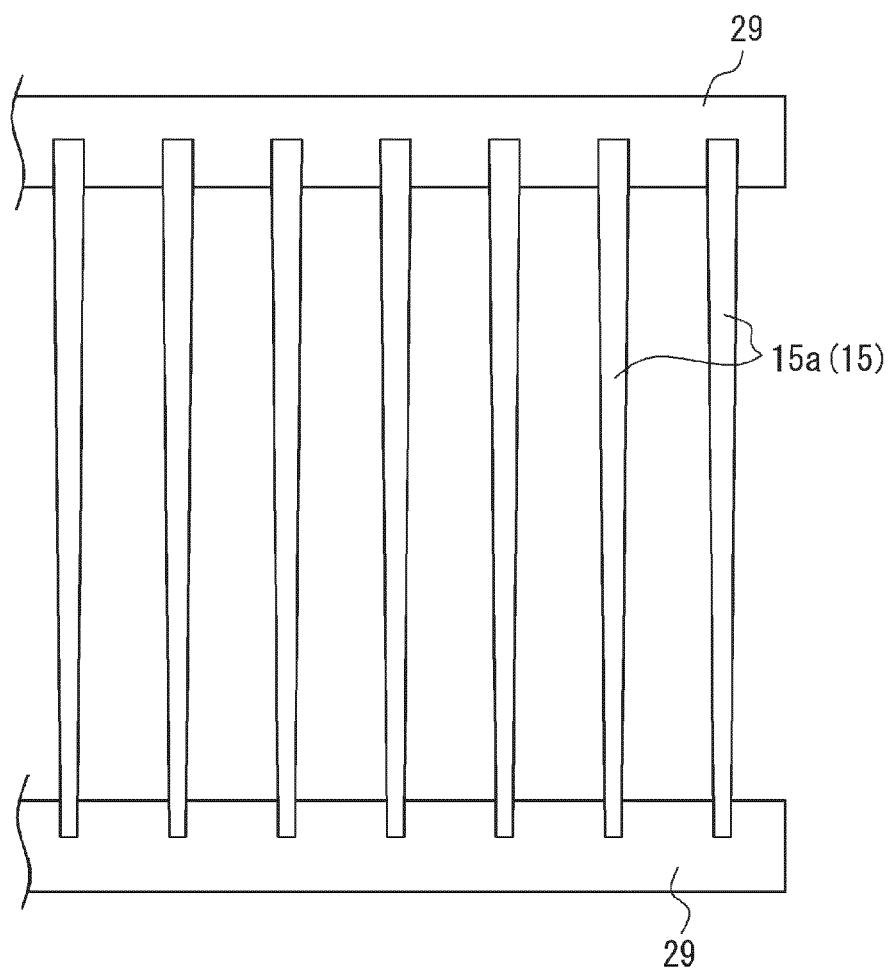
FIG. 13 is a diagram illustrating a separation step of the method of manufacturing a puncture needle illustrated in FIG. 8.

In the separation step, the tubular bodies 15a are successively separated from the sheet member 16. In this step, each of the tubular bodies 15a is separated from a boundary portion between the tubular body 15a and a pair of connection portions 27. A method of separating the tubular body 15a from the sheet member 16 is not particularly limited, and, for example, the tubular body 15a may be mechanically cut out or cut out by a laser or the like. Further, in the separation step, at substantially the same time or after the separation of the tubular body 15a, the tubular bodies 15a are temporarily fixed to hold a positional relationship between the tubular bodies 15a. In the present embodiment, the temporary fixation is performed by sticking both end portions of the tubular body 15a to a pair of adhesive tapes (temporary fixation member) 29 (performed by sticking at least a portion excluding a longitudinal center portion of the tubular body 15a to the adhesive tape 29), as illustrated in FIG. 13.

An interval between the tubular bodies 15a temporarily fixed adjacently is not particularly limited (interval is not indispensable), and is appropriately set according to conditions, but the interval is preferably set smaller than an interval between adjacent tubular bodies 15a partially connected to the sheet member 16. Therefore, the tubular bodies 15a can be closely arranged, the bevels can be formed simultaneously for a large number of tubular bodies 15a in the next step (bevel forming step), and productivity thereof can be improved. The interval between the tubular bodies 15a temporarily fixed adjacently can be arbitrarily adjusted by adjusting a movement rate of the adhesive tape 29 (feed pitch). For example, in order to reduce the interval between the tubular bodies 15a temporarily fixed adjacently relative to the interval between adjacent tubular bodies 15a partially connected to the sheet member 16, the movement rate of the adhesive tape 29 during applying a tubular body 15a and a subsequent tubular body 15a to the adhesive tape 29 is set smaller than the pitch between the tubular bodies 15a partially connected to the sheet member 16 (movement rate of the sheet member 16 during separating a tubular body 15a and a subsequent tubular body 15a).

[Bevel Forming Step]

In the bevel forming step, the bevel is formed at least at one end of each tubular body 15a as the linear member 15 to form the needle tip, and the puncture needle 1' is formed. In this step, while the positional relationship is held between the tubular bodies 15a, the bevels are simultaneously formed to the tubular bodies 15a. As described above, since the bevels are formed while the positional relationship is held between the tubular bodies 15a, the bevels can be formed readily, surely, and accurately, and since the bevels are formed simultaneously to the tubular bodies 15a, productivity thereof can be improved.

Figure 14A:
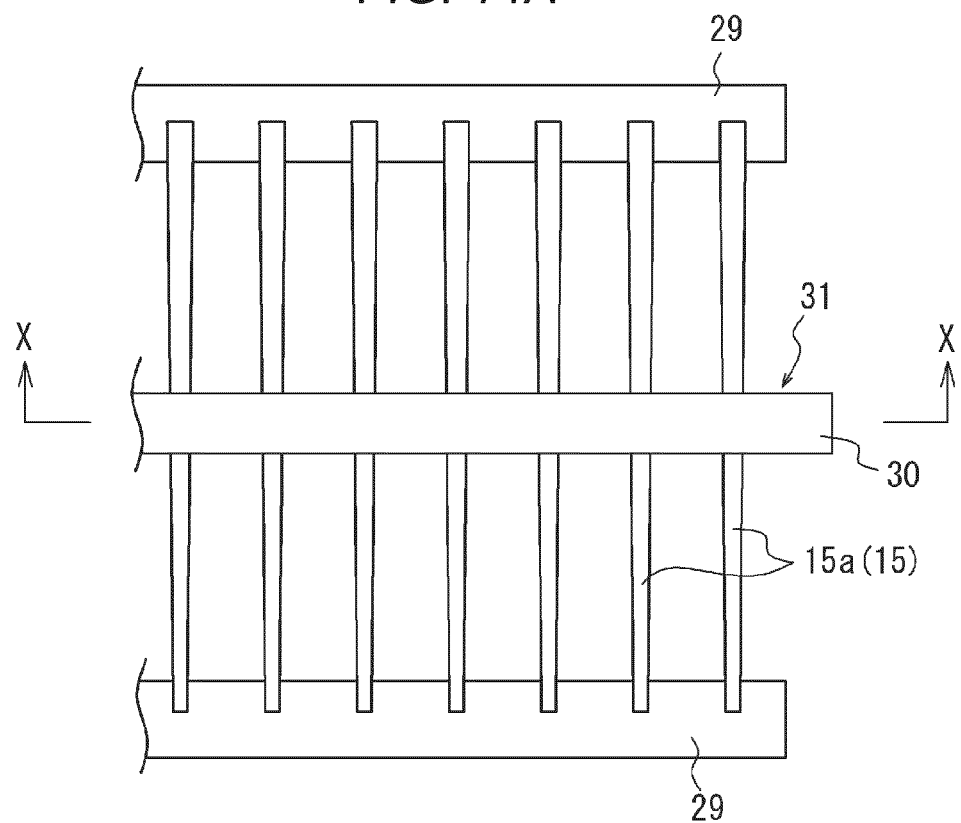
FIGS. 14A and 14B are diagrams illustrating a bevel forming step of the method of manufacturing a puncture needle illustrated in FIG. 8.
Figure 14B:
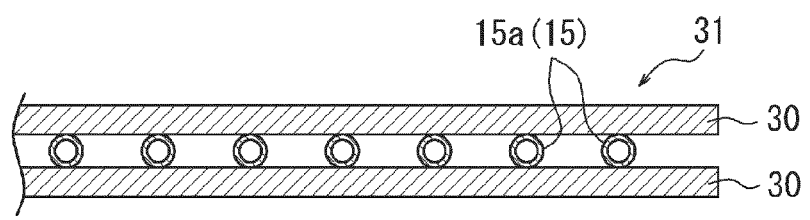

In the present embodiment, substantially the longitudinal center portions of the tubular bodies 15a are held to hold the positional relationship between the tubular bodies 15a, in the bevel forming step. That is, as illustrated in FIGS. 14A and 14B, a holding mechanism 31 has a pair of elongated grip portions (holding portions) 30 for gripping (holding) the substantially center portions of the tubular bodies 15a, and directly holds the positional relationship between the tubular bodies 15a stuck to a pair of the adhesive tapes 29 for temporary fixation. Then, at a portion of one end of each tubular body 15a (upper side in FIG. 14A) that is not stuck to the adhesive tape 29, an end portion 3' is formed which includes a first bevel 5', a second bevel 6', and an inclined surface (third bevel) 7' (see FIG. 15). Thus, the adhesive tapes 29 are removed from the puncture needle 1' in which the end portion 3' is formed. Note that a portion of the other end (lower side in FIG. 14B) that is not stuck to the adhesive tape 29 may be processed to form a bevel.

For a method of forming a bevel at the end portion 3', that is, for a method of forming the first bevel 5', the second bevel 6', and the inclined surface 7', the wire cutting such as wire electric discharge machining is employed. According to such a method, the end portion having a bevel of desired shape can be formed readily and surely.

The method of forming the first bevel 5', the second bevel 6', and the inclined surface 7' according to the present embodiment will be described here in detail. In the present embodiment, first, the inclined surface 7' is formed by wire cutting. Specifically, the tubular body 15a as the linear member 15 having a substantially circular cross-sectional outer shape is moved with respect to a wire in one direction inclined relative to the axial direction A by a predetermined angle (see FIG. 15) to form the inclined surface 7'. Note that the predetermined angle is determined based on an angle of the inclined surface 7' relative to the axial direction A.

Next, when the wire reaches an edge of the opening 11' after forming the inclined surface 7' (see FIG. 15) (when the wire reaches a position serving as a ridge 12' after completion of the puncture needle 1' (see FIG. 15)), the linear member 15 is rotated in one direction about the axis O of the linear member 15 (see FIG. 15), and moved in the one direction inclined relative to the axial direction A by the predetermined angle which is the same as the direction in which the tubular body 15a is moved upon forming the inclined surface 7, and in such a state, the first bevel 5' is formed at one end portion of the linear member 15 by wire cutting.

That is, when the inclined surface 7' is formed, the linear member 15 is not rotated about the axis O, but is merely moved at a predetermined constant rate in the one direction inclined relative to the axial direction A by the predetermined angle. Then, when the wire reaches a predetermined position where formation of the inclined surface 7 is completed, circumferential rotation about the axis O is started in addition to the movement at the constant rate in the one direction inclined relative to the axial direction A by the predetermined angle, and the first bevel 5' is formed following the formation of the inclined surface 7'. In the present embodiment, the rod-shaped member 15 is rotated counterclockwise to form the first bevel 5'. Further the rod-shaped member 15 is rotated at a predetermined constant rotation speed.

As described above, in the present embodiment, the inclined surface 7' and the first bevel 5' can be formed by single wire cutting.

Further, in the present embodiment, the linear member 15 is rotated in an opposite direction about the axis O (clockwise direction in the present embodiment), and moved in the one direction inclined relative to the axial direction A by the predetermined angle or in a direction opposite to the one direction, and in such a state, the second bevel 6' is formed by wire cutting, at a position of the one end portion different from the position of the first bevel 5'. Still further, the second bevel 6' is formed, and an cutting edge 9' is formed. The cutting edge 9' is constituted by the ridge formed where the first bevel 5' and the second bevel 6' intersect, and has a needle tip 8'. Note that the linear member 15 is moved in the one direction inclined relative to the axial direction A by the predetermined angle or in the direction opposite to the one direction, at a speed equal to the moving speed of the linear member 15 during formation of the first bevel 5'. Furthermore, the linear member 15 is rotated about the axis O at a speed equal to the rotation speed of the linear member 15 during formation of the first bevel 5'.

Specifically, after a first wire cutting process in which the inclined surface 7' and the first bevel 5' are formed, the second bevel 6' is formed by a second wire cutting process. When the second bevel 6' is formed, the cutting edge 9' constituted by the ridge formed where the first bevel 5' and the second bevel 6' intersect is simultaneously formed to form all the bevels at the end portion 3' of the puncture needle 1' by cutting twice in the first and second wire cutting processes, and a time required for the bevel forming step for the end portion 3' can be reduced.

Here, the second wire cutting process for forming the second bevel 6' can be performed by any of the following two methods. A first method is a method for forming the second bevel 6' from the cutting edge tip 8' side to the inclined surface 7' side, and a second method is a method for forming the second bevel 6' from the inclined surface 7' side to the cutting edge tip 8' side.

When the first method is used, the linear member 15 is rotated in the clockwise direction about the axis O, and moved in the direction opposite to the one direction inclined relative to the axial direction A by the predetermined angle, and the second bevel 6' is formed by the second wire cutting process. When the second method is used, the linear member 15 is rotated in the clockwise direction about the axis O, and moved in a direction the same as the one direction inclined relative to the axial direction A by the predetermined angle, and the second bevel 6' is formed by the second wire cutting process. Since the second wire cutting process can be performed sequentially after the first wire cutting process in the first method, the first method is performed more efficiently than the second method.

Note that in the present embodiment, a method for moving the tubular body 15a as the linear member 15 with respect to the wire for wire cutting has been described, but a method for moving the wire with respect to the linear member 15 may be adopted. However, moving the linear member 15 for wire cutting is preferably adopted for easy operation.

[Polishing Step]

The puncture needle 1' including the end portion 3' in which the first bevel 5', the second bevel 6', and the inclined surface 7' are formed is polished in the polishing step. For polishing, the ion etching is employed. The puncture needle 1' is ion-etched with argon as a medium, using a plasma ion gas in a vacuum atmosphere. According to such polishing, burrs caused in wire electric discharge machining can be fused and vaporized, and the puncture needle 1' including the end portion 3' having the first bevel 5', the second bevel 6', the inclined surface 7', the needle tip 8', and the cutting edge 9' which are formed in desired shapes can be polished relatively readily and surely.

Further, at the same time, dirt caused by metal or the like adhering to a processed surface during wire electric discharge machining can be also removed.

The puncture needle 1' can be manufactured by the steps as described above. In the present embodiment, the method of manufacturing the puncture needle 1' has been described, but the puncture needle 1 according to the first embodiment can be also manufactured by a similar method. Furthermore, the puncture needles 100 and 300 according to the second and fourth embodiments can be also manufactured using a similar method. However, since the needle tips 80 and 82 are configured not to be positioned on the axial plane X, the moving speed or rotation speed of the tubular body 15a during forming the first bevel may be made different from the moving speed or rotation speed of the tubular body 15a during forming the second bevel to form asymmetric bevels, in the above-mentioned bevel forming step.

Furthermore, since the puncture needle 200 according to the third embodiment is the solid needle, the reception step, the press forming step (see FIGS. 9 to 12), the bonding step, the straightening step, and the separation step (see FIG. 13) are not required. Thus, the puncture needle 200 can be manufactured by performing the bevel forming step (see FIGS. 14A and 14B) and the polishing step on a solid rod-shaped member 15.

The present invention relates to a medical puncture needle and a method of manufacturing a puncture needle.

REFERENCE SIGNS LIST

1, 1', 100, 200, 300 Puncture needle
2, 102, 202, 302 Main body portion
3, 3', 103, 203, 303 End portion
5, 5', 50, 51, 52, 53 First bevel (Bevel)
6, 6', 60, 61, 62, 63 Second bevel (Bevel)
7, 7', 70, 71, 72, 73 Inclined surface (Bevel)
8, 8', 80, 82, 83 Needle tip
9, 9', 90, 92, 93 Cutting edge
10, 104, 304 Hollow portion
11, 11', 111, 311 Opening
12, 12' Ridge
120a, 120b Connecting position
13 Inner edge of first bevel
14 Inner edge of second bevel
15 Rod-shaped member
15a Tubular body
16 Sheet member
17 Blank
18 Recessed die (die) of first bending unit
19 Projecting die (die) of first bending unit
20 First bending unit
21 Recessed die (die) of second bending unit
22 Projecting die (die) of second bending unit
23 Second bending unit
24, 25 Third bending unit pair of recessed dies (dies)
26 Third bending unit
27 Connection portion
28 Seam
29 Adhesive tape (Temporary fixation member)
30 Grip portion (Holding portion)
31 Holding mechanism
204 Straight portion
205 Curved portion
A Axial direction
B Direction orthogonal to axial direction (orthogonal direction)
O Axis
X Plane perpendicular to inclined surface and including axis (Axial plane)
Y Plane including first cutting edge and axis
θ Angle relative to axial plane in cross-section orthogonal to axial direction
θ1-θ9 Angle of second bevel relative to axial plane in cross-section orthogonal to axial direction

What is claimed is:

1. A method of manufacturing a medical puncture needle comprising:
   providing a tubular body having a substantially circular cross-sectional outer shape, which comprises:
      punching a blank from a sheet member such that the blank remains partially connected to the sheet member,
      while the blank remains partially connected to the sheet member, bending the blank into a tubular shape using at least one projecting die and at least one recessed die,
      while the tubular-shaped blank remains partially connected to the sheet member, bonding a seam between adjacent edges of the tubular-shaped blank to form the tubular body, and
      separating the tubular body from the sheet member while the tubular body is temporarily fixed to a temporary fixation member that comprises adhesive tape; and
   forming a first bevel at an end portion of the tubular body by machining the tubular body while (i) rotating the tubular body about an axis of the tubular body in a first rotation direction, and (ii) moving the tubular body in a first direction that is inclined by a predetermined angle relative to the axis of the tubular body.

2. The method according to claim 1, further comprising:
forming a second bevel and a cutting edge at the end portion of the tubular body by machining the tubular body while (i) rotating the tubular body about the axis in a direction opposite to the first rotation direction, and (ii) moving the tubular body in the first direction,
wherein the second bevel is formed at a position of the end portion different from a position of the first bevel, and
wherein the cutting edge is constituted by a ridge formed where the first and second bevels intersect, the ridge defining a needle tip at one end thereof.

3. The method according to claim 2, wherein a rotation speed at which the tubular body is rotated during the step of forming the second bevel is equal to a rotation speed at which the tubular body is rotated during the step of forming the first bevel.

4. The method according to claim 1, further comprising:
forming a second bevel and a cutting edge at the end portion of the tubular body by machining the tubular body while (i) rotating the tubular body about the axis in a direction opposite to the first rotation direction, and (ii) moving the tubular body in a direction opposite to the first direction,
wherein the second bevel is formed at a position of the end portion different from a position of the first bevel, and
wherein the cutting edge is constituted by a ridge formed where the first and second bevels intersect, the ridge defining a needle tip at one end thereof.

5. The method according to claim 4, wherein a rotation speed at which the tubular body is rotated during the step of forming the second bevel is equal to a rotation speed at which the tubular body is rotated during the step of forming the first bevel.

6. The method according to claim 1, further comprising:
before forming the first bevel, forming an inclined surface at the end portion of the tubular body by machining the tubular body while moving the tubular body in the first direction that is inclined by the predetermined angle relative to the axis of the tubular body.

7. The method according to claim 2, further comprising:
after forming the first and second bevels, polishing the tubular body using an ion etching process.

8. The method according to claim 1, wherein:
the step of bending the blank comprises:
bending the blank a first time using a first projecting die and a first recessed die, and
bending the blank a second time using a second projecting die and a second recessed die.

9. The method according to claim 8, wherein:
the step of bending the blank further comprises:
bending the blank a third time using a third recessed die and a fourth recessed die.

10. The method according to claim 9, wherein:
the step of bending the blank the third time is performed while a core is positioned in a hollow portion of the tubular body.

11. The method according to claim 1, wherein:
the step of bonding the seam between adjacent edges of the tubular body is performed using a welding process.

12. The method according to claim 11, wherein:
the welding process is a laser welding process using a carbon dioxide laser, a YAG laser, or an excimer laser.

13. The method according to claim 1, wherein:
the tubular body has an inner diameter that gradually decreases from a first end to a second end of the tubular body.

14. The method according to claim 1, wherein:
the step of providing the tubular body further comprises:
straightening the tubular body by pressing the tubular body between a pair of rollers.

15. The method according to claim 1, further comprising:
gripping the tubular body with a grip portion; and
removing the temporary fixation member from at least one end of the tubular body;
wherein the tubular body is held by the grip portion while the first bevel is formed.

16. A method of manufacturing a medical puncture needle comprising:
providing a tubular body having a substantially circular cross-sectional outer shape, which comprises:
punching a blank from a sheet member such that the blank remains partially connected to the sheet member,
while the blank remains partially connected to the sheet member, bending the blank into a tubular shape using at least one projecting die and at least one recessed die,
while the tubular-shaped blank remains partially connected to the sheet member, bonding a seam between adjacent edges of the tubular-shaped blank to form the tubular body, and
separating the tubular body from the sheet member while the tubular body is temporarily fixed to a temporary fixation member;
gripping the tubular body with a grip portion;
removing the temporary fixation member from at least one end of the tubular body; and
while the tubular body is held by the grip portion, forming a first bevel at an end portion of the tubular body by machining the tubular body while (i) rotating the tubular body about an axis of the tubular body in a first rotation direction, and (ii) moving the tubular body in a first direction that is inclined by a predetermined angle relative to the axis of the tubular body.

\* \* \* \* \*